United States Patent
Orme et al.

(10) Patent No.: US 6,962,918 B2
(45) Date of Patent: Nov. 8, 2005

(54) HEXAHYDROPYRAZINO[1'2';1,6]PYRIDO[3,4-B]INDOLE-1,4-DIONES FOR THE TREATMENT OF CARDIOVASCULAR DISORDERS AND ERECTILE DYSFUNCTION

(75) Inventors: Mark W. Orme, Seattle, WA (US); Lisa M. Schultze, Woodinville, WA (US); Jason Scott Sawyer, Indianapolis, IN (US); Alain Claude-Marie Daugan, Les Ulis (FR); Raymond Brown, Fishers, IN (US)

(73) Assignee: Lilly Icos LLC., Wilmington, DE (US)

( * ) Notice: Subject to any disclaimer, the term of this patent is extended or adjusted under 35 U.S.C. 154(b) by 127 days.

(21) Appl. No.: 10/363,569

(22) PCT Filed: Sep. 17, 2001

(86) PCT No.: PCT/US01/28972

§ 371 (c)(1),
(2), (4) Date: Feb. 27, 2003

(87) PCT Pub. No.: WO02/28858

PCT Pub. Date: Apr. 11, 2002

(65) Prior Publication Data

US 2003/0236263 A1 Dec. 25, 2003

Related U.S. Application Data

(60) Provisional application No. 60/237,477, filed on Oct. 2, 2000.

(51) Int. Cl.[7] .................. C07D 471/14; C07D 487/14; A61K 31/4985; A61P 9/12; A61P 15/10
(52) U.S. Cl. ....................................... 514/250; 544/343
(58) Field of Search .......................... 544/343; 514/250

(56) References Cited

U.S. PATENT DOCUMENTS

| | | | | |
|---|---|---|---|---|
| 5,859,006 A | * | 1/1999 | Daugan | 514/249 |
| 5,981,527 A | * | 11/1999 | Daugan et al. | 514/250 |
| 6,140,329 A | * | 10/2000 | Daugan | 514/250 |

FOREIGN PATENT DOCUMENTS

| | | |
|---|---|---|
| WO | WO 95/19978 | 7/1995 |
| WO | WO 97/03675 | 2/1997 |
| WO | WO 9703675 A1 * | 2/1997 |
| WO | WO 97/03985 | 2/1997 |
| WO | WO 02/11706 | 2/2002 |

OTHER PUBLICATIONS

Wang et al., Organic Letters vol. 1 (10) 1647–1649, 1999.*
Lucas et al. Pharmacological Reviews 52 (3), 375–413, 2000.*
West, Anthony R., Solid State Chemistry and its Applications, Wiley, New York, 1988, pp. 358 & 365.*
A. Madrigal et al., *Tetrahedron: Asymmetry 11*, 3515–3526 (2000).
H. He et al., *Med. Chem. Res.*, 9:6, 424–437 (1999).
H. Wang et al., *Org. Lett.*, vol. 1, No. 10, 1647–1649 (1999).
S. Edmondson et al., *J. Am. Chem. Soc., 121*, 2147–2155 (1999).
A. van Loevezijn et al., *Tetrahedron Letters, 39*, 4737–4740 (1998).
A. Madrigal et al., *Tetrahedron: Asymmetry 9*, 3115–3123 (1998).
S.K. Pandey et al., *Tetrahedron, 57*, 4437–4442 (2001).

* cited by examiner

Primary Examiner—Venkataraman Balasubramanian
(74) Attorney, Agent, or Firm—Marshall, Gerstein & Borun LLP

(57) ABSTRACT

Compounds of the general structural formula (I), and use of the compounds and salts and solvates thereof, as therapeutic agents.

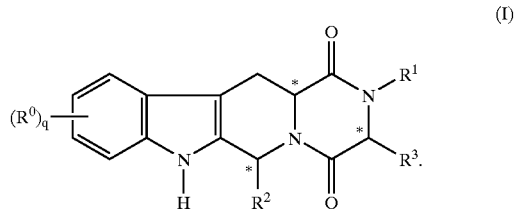

18 Claims, No Drawings

HEXAHYDROPYRAZINO[1'2';1,6]PYRIDO[3,4-B]INDOLE-1,4-DIONES FOR THE TREATMENT OF CARDIOVASCULAR DISORDERS AND ERECTILE DYSFUNCTION

"This application is a 371 of PCT/US01/28972, filed Sep. 17, 2001, which claims benefit of provisional U.S. patent application 60/237,477, filed Oct. 2, 2000".

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

DETAILED DESCRIPTION OF THE INVENTION

The present invention provides compounds of formula (I)

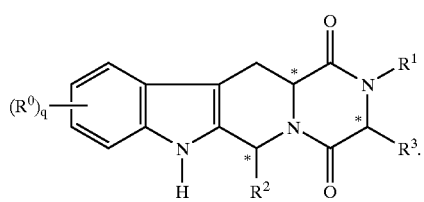

(I)

wherein $R^0$, independently, is selected from the group consisting of halo and $C_{1-6}$alkyl;

$R^1$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, and heteroaryl$C_{1-3}$alkyl;

$R^2$ is selected from the group consisting of hydrogen, $C_{1-6}$alkyl, aryl$C_{1-3}$alkyl, $C_{1-3}$alkenylaryl, halo$C_{1-6}$alkyl, $C_{1-4}$alkyleneC(=O)OR$^a$, $C_{1-4}$alkyleneC(=O)—NR$^a$R$^b$, $C_{3-8}$cycloalkyl, Het, $C_{3-8}$cycloalkenyl, $C_{3-8}$heterocycloalkenyl, $C_{1-4}$alkyleneHet, $C_{1-4}$alkyleneQR$^a$, $C_{2-6}$alkenyleneQR$^a$, $C_{1-4}$alkyleneQC$_{1-4}$alkyleneQR$^a$,

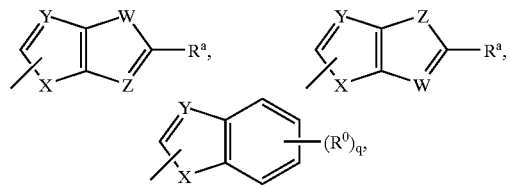

and a Spiro substituent having the structure

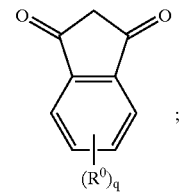

$R^3$ is selected from the group consisting of hydrogen and $C_{1-6}$alkyl, or $R^1$ and $R^3$ together represent a 3- or 4-membered alkyl or alkenyl chain component of a 5- or 6-membered ring;

$R^a$ and $R^b$, independently, are selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, $C_{1-3}$alkyleneheteroaryl, and Het;

$R^c$ is null or is selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, $C_{1-3}$alkyleneheteroaryl, and Het;

Het is a 5- or 6-membered heterocyclic group, saturated or partially unsaturated, containing at least one heteroatom selected from the group consisting of oxygen, nitrogen, and sulfur, and optionally substituted with $C_{1-4}$alkyl or C(=O)OR$^a$;

Q is O, S, or NR$^a$;
W is O, S, or NR$^c$;
X is O, S, or NR$^a$;
Y is CR$^a$ or N;
Z is CR$^a$, C(R$^a$)$_2$, or NR$^c$; and
q is 0, 1, 2, 3, or 4.

As used herein, the term "alkyl" includes straight chained and branched hydrocarbon groups containing the indicated number of carbon atoms, typically methyl, ethyl, and straight chain and branched propyl and butyl groups. The term "alkyl" includes "bridged alkyl," i.e., a $C_6$–$C_{16}$ bicyclic or polycyclic hydrocarbon group, for example, norbornyl, adamantyl, bicyclo[2.2.2]octyl, bicyclo[2.2.1]-heptyl, bicyclo[3.2.1]octyl, or decahydronaphthyl. The term "cycloalkyl" is defined as a cyclic $C_3$–$C_8$ hydrocarbon group, cyclopropyl, cyclobutyl, cyclohexyl, and cyclopentyl. The terms "alkenyl" and "alkynyl" are defined similarly to the term "alkyl," except the hydrocarbon group contains a carbon-carbon double bond or carbon-carbon triple bond, respectively. "Cycloalkeny" is defined similarly to cycloalkyl, except a carbon-carbon double bond is present in the ring. The hydrocarbon group can contain up to 16 carbon atoms.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "aryl$C_{1-3}$alkyl" and "heteroaryl$C_{1-3}$alkyl" are defined as an aryl or heteroaryl group having a $C_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" includes a 5- or 6-membered heterocycloalkyl group exemplified by morpholinyl, piperidyl, pyrrolidinyl, or piperazinyl.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly, except a sulfur atom, rather than an oxygen atom, is present.

The term "hydroxy" is defined as —OH.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, where R is alkyl.

The term "alkylsulfinyl" is defined as R—SO$_2$, where R is alkyl.

The term "alkylsulfonyl" is defined as R—SO$_3$, where R is alkyl.

The term "nitro" is defined as —NO$_2$.

The term "trifluoromethyl" is defined as —CF$_3$.

The term "trifluoromethoxy" is defined as —OCF$_3$.

The term "cyano" is defined as —CN.

The term "spiro" as used herein refers to a group having two carbon atoms directly bonded to the carbon atom to which R$^2$ is attached.

In preferred embodiments, R$^2$ is optionally substituted and selected from the group consisting of $C_{1-4}$alkyleneQR$^a$, $C_{1-4}$alkyleneQC$_{1-4}$alkyleneQR$^a$, $C_{3-8}$cycloalkyl, $C_{3-8}$cycloalkenyl, $C_{1-6}$alkyl,

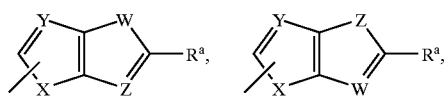

-continued

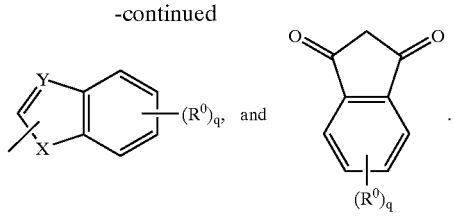

In a more preferred group of compounds of formula (I), R$^2$ is represented by

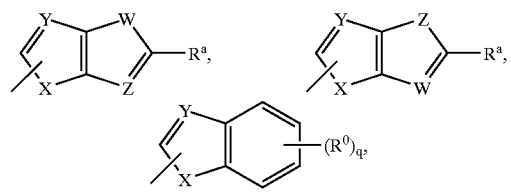

$C_{3-8}$cycloalkyl, $C_{3-8}$cycloalkenyl, $C_{1-6}$alkyl, $C_{1-4}$alkyleneQR$^a$, and $C_{1-4}$alkyleneQC$_{1-4}$alkyleneQR$^a$. A preferred Q is oxygen.

Especially preferred R$^2$ substituents include

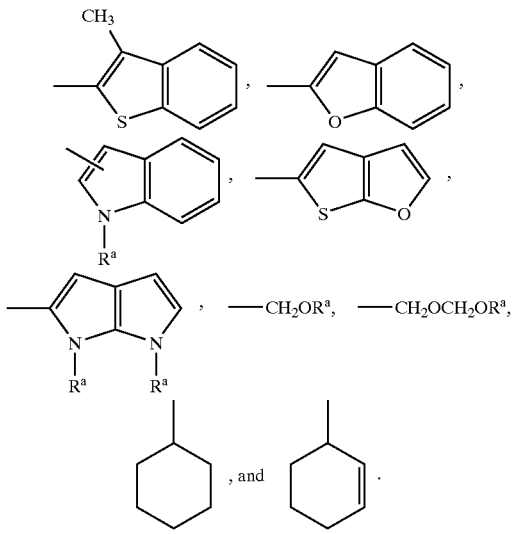

Within this particular group of compounds, preferred R$^a$ substituents include hydrogen, $C_{1-6}$alkyl, and benzyl.

An especially preferred subclass of compounds within the general scope of formula (I) is represented by compounds of formula (II)

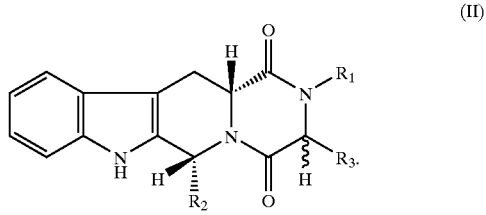

(II)

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of the formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5 to about 95% compound of the present invention, and preferably from about 25 to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5 to about 90% by weight of a compound of the present invention, and preferably about 1 to about 50% of a compound of the present invention.

When a therapeutically effective amount of a compound of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents, such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, and $R^3$ are as defined in structural formula (I) above. In particular, Daugan U.S. Pat. No. 5,859,006, incorporated herein by reference, discloses preparation of a compound of structural formula (III).

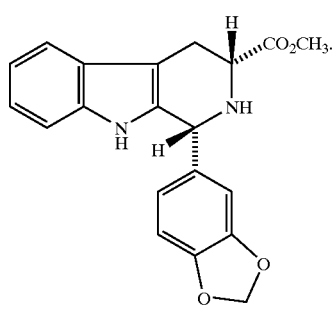

In short, the compound of structural formula (III), i.e., the cis-isomer of Intermediates 1 and 2 of Daugan U.S. Pat. No. 5,859,006 was prepared according to the following reaction scheme:

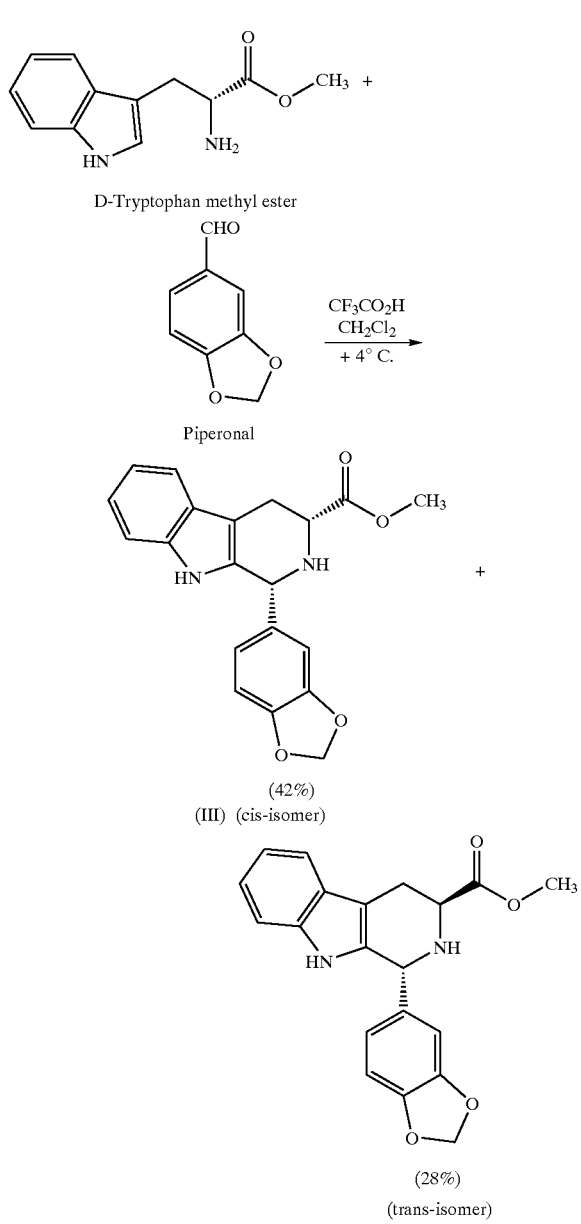

A compound of structural formula (I) is prepared similarly by reacting a tryptophan ester, or a tryptophan ester substituted with suitable $R^0$ substituents, with a suitable aldehyde to provide the desired $R^2$ substituent. The resulting product then is cyclized by reaction with a suitable amine to provide a compound of structural formula (I). The cyclization reaction is disclosed in Daugan U.S. Pat. No. 5,859,006.

In the synthesis of compounds of structural formula (I), protecting compounds and protecting groups, like benzyl chloroformate and trichloroethyl chloroformate, which are well known to persons skilled in the art, can be used. Such protecting groups are disclosed, for example, in T. W. Greene et al., "Protective Groups in Organic Synthesis, Third Edition," John Wiley and Sons, Inc., NY, N.Y. (1999). The structure of a compound of structural formula (I) can be varied by using an appropriate aldehyde to change the identity of $R^2$, or by using a halo or alkyl phenyl-substituted tryptophan ester.

Compounds of formula (I) can be converted to other compounds of formula (I). Thus, for example, when a compound contains a substituted aromatic ring, it is possible to prepare another suitably substituted compound of formula (I). Examples of appropriate interconversions include, but are not limited to, $OR^a$ to hydroxy by suitable means (e.g., using an agent such as $SnCl_2$ or a palladium catalyst, such as palladium-on-carbon), or amino to substituted amino, such as alkylamine, using standard acylating or sulfonylating conditions.

Compounds of formula (I) can be prepared by the method above as individual stereoisomers from the appropriate stereoisomer of formula (III) or as a racemic mixture from the appropriate racemic compound of formula (III). Individual stereoisomers of the compounds of the invention can be prepared from racemates by resolution using methods known in the art for the separation of racemic mixtures into their constituent.'stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided.

The following abbreviations are used hereafter in the accompanying examples: rt (room temperature), min (minute), h (hour), g (gram), mmol (millimole), m.p. (melting point), eq (equivalents), L (liter), mL (milliliter), µL (microliters), DMSO (dimethyl sulfoxide), $CH_2Cl_2$ (dichloromethane): $CHCl_3$ (chloroform), TFA (trifluoroacetic acid), EtOH (ethanol), MeOH (methanol), $Et_3N$ (triethylanine), $MeNH_2$ (methylamine), DMF (dimethylformamide), EtOAc (ethyl acetate), $S_8$ (sulfur), DIPEA (diisopropylethylamine), MOM-Cl (chloromethyl methyl ether), TSOH (p-toluene-sulfonic acid), $NaHCO_3$ (sodium bicarbonate), $Na_2SO_4$ (sodium sulfate), AcOH (acetic acid), HCl (hydrochloric acid), $LiAH_4$ (lithium aluminum hydride), $Et_2O$ (diethyl ether), PCC (pyridinium chlorochromate), $Al_2O_3$ (aluminum oxide), i-PrOH (isopropyl alcohol), and THF (tetrahydrofuran).

General Synthesis of a Compound of Formula (I)

The following sequence illustrates a general route to compounds of structural formula (I) wherein $R^2$ is

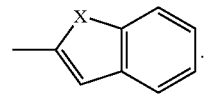

Similar synthetic routes can be used to synthesize other compounds of structural formula (I).

The general synthetic-route is analogous to the route disclosed in U.S. Pat. No. 5,859,006, incorporated by reference. In particular, a tryptophan ester (IV) is subjected to a Pictet-Spengler reaction with an appropriate aldehyde, such as (V) for example, in the presence of trifluorocetic acid (TFA) to provide a β-carboline (VI). Acylation with. chloroacetyl chloride provides an N-derivatized compound (VII), which in turn is treated a desired primary amine ($RNH_2$) to provide a diketopiperazine compound (VIII) of structural formula (I).

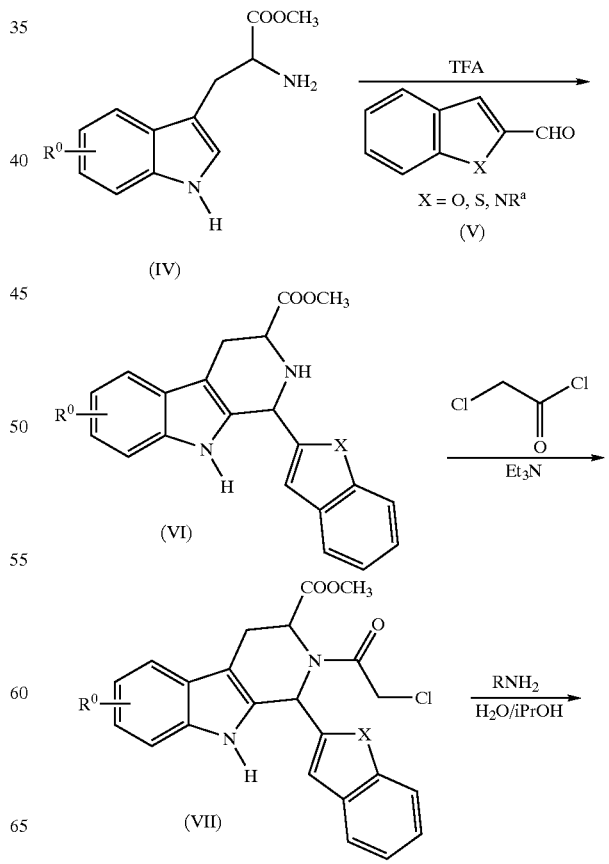

-continued

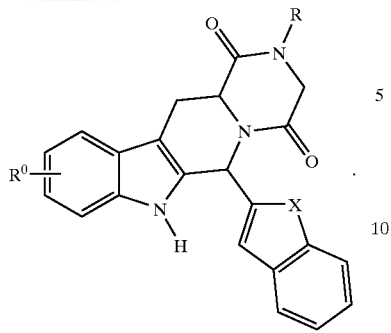

The following illustrates specific examples of compounds of structural formula (I) and synthetic routes to some of these structures.

PREPARATION OF EXAMPLES 1–14

The following Examples 1–14 were prepared by the above-described general synthetic scheme. The details of each step in the above synthetic scheme are disclosed in U.S. Pat. No. 5,849,006.

PREPARATION OF EXAMPLE 1

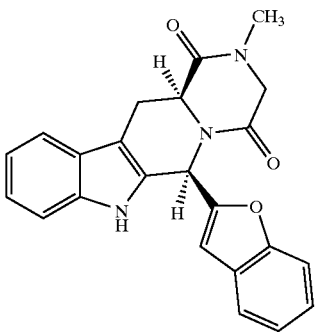

EXAMPLE 1

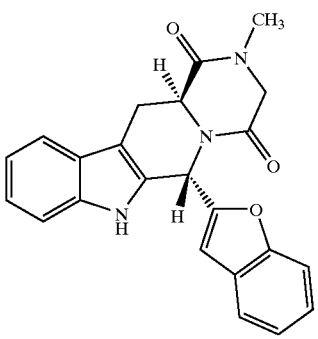

EXAMPLE 2

EXAMPLE 1 was prepared from the following Intermediate 1. Example 2 was prepared from the following Intermediate 2.

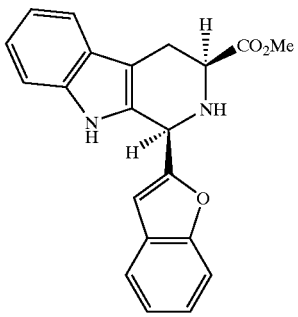

Intermediate 1

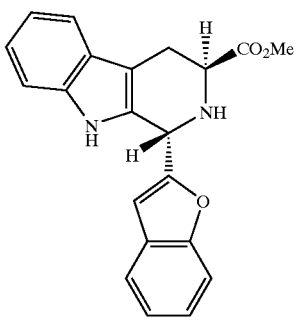

Intermediate 2

Preparation of (1R,3S)- and (1S,3S)-1-benzofuran-2-yl-2,3,4,9-tetrahydro-1-H-β-carboline-3-carboxylic acid methyl ester (Intermediates 1 and 2)

Using benzofuran-2-carbaldehyde as the starting aldehyde, Intermediates 1 and 2 were prepared by the same method described below for (1R,3S)- and (1S,3S)-1-(3-methyl-benzo[b]thiophen-2-yl)-2,3,4,9-tetrahydro-1H-β-carboline-3-carboxylic acid methyl ester (Intermediates 3 and 4). The crude mixture of diastereomers was separated by chromatography (Chiralcel OD-H column, 60% heptane, 40% ethanol) to yield 2.5 g (56%) of (1R,3S)-1-benzofuran-2-yl,2,3,4,9-tetrahydro-1H-β-carboline-3-carboxylic acid methyl ester (Intermediate 1) and 920 mg (20%) of (1S,3S)-1-benzofuran-2-yl-2,3,4,9-tetrahydro-1H-β-carboline-3-carboxylic acid methyl ester (Intermediate 2) as foams.

(1R,3S)-1-Benzofuran-2-yl-2,3,4,9-tetra-hydro-1H-β-carboline-3-carboxylic acid methyl ester (Intermediate 1): $^1$H NMR (DMSO-$d_6$): δ10.9 (s, 1H), 7.6–6.95 (m, 8H), 6.56 (s, 1H), 5.52 (d, J=4 Hz, 1H), 3.93 (m, 1H), 3.7 (s, 3H), 3.06 (dd, J=5.15 Hz, 1H), 2.8 (dd, J=10.15 Hz, 1H); MS ES+m/e 347.2 (p+1), ES−m/e 345.2 (p−1).

(1S,3S)-1-Benzofuran-2-yl-2,3,4,9-tetra-hydro-1H-β-carboline-3-carboxylic acid methyl ester (Intermediate 2). $^1$H NMR (DMSO-$d_6$): δ10.66 (s, 1H), 7.7–6.95 (m, 8H), 6.9 (s, 1H), 5.55 (d, J=6 Hz, 1H), 3.9 (m, 1H), 3.64 (s, 3H), 3.05 (m, 1H), 2.85 (dd, J=2.10 Hz, 1H); MS ES+m/e 347.2 (p+1), ES−m/e 345.2 (p−1).

Preparation of (6R,12aS)-6-benzofuran-2-yl-2-methyl-2,3,6,7,12,12a-hexahydro-pyrazino [1',2':1,6]pyrido[3,4-b]indole-1,4-dione (Example 1)

Example 1 was prepared from Intermediate 1 (2.66 mmol), triethylamine (1 mL), and chloroacetyl chloride (2.7 mmol) in tetrahydrofuran (25 mL). The mixture was stirred for 18 hours without cooling. The mixture then was diluted with ethyl acetate, washed once with water, once with 1 N hydrochloric acid, once with saturated sodium chloride solution, then dried (sodium sulfate), filtered, and concentrated in vacuo. The crude material was purified by chromatography (silica gel, 50%.ethyl acetate, 50% hexanes, then ethyl acetate) to provide 852 mg (30%) of Example 1 as a solid: mp 195–198° C. ¹H NMR (DMSO-d₆): δ11.6 (s, 1H), 7.65–7.0 (m, 9H), 4.4 (dd, J=4.13 Hz, 1H), 4.2 (ABq, J=18.65 Hz), 3.32 (dd, J=4.13 Hz, 1H), 3.05 (dd, J=13.5 Hz, 1H), 2.82 (s, 3H), MS ES+m/e 386.3(p+1), ES−m/e 384.3 (p−1); IR (KBr, cm⁻¹) 1729, 1663, 1462.

Example 2 was prepared by the same method as Example 1 from Intermediate 2.

Preparation of Example 3

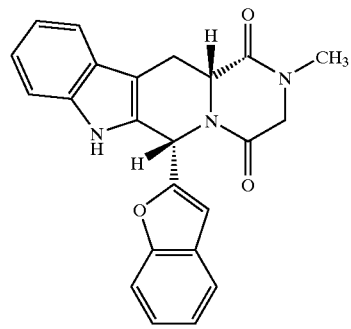

Example 3, (6S,12aR)-6-benzofuran-2-yl-2-methyl-2,3,6,7,12,12a-hexahydropyrazino[1',2':1,6]-pyrido[3,4-b]indole-1,4-dione, was prepared from Intermediate 3 by the same method set forth above for Example 1. The crude material was purified by chromatography (silica gel, 30% ethyl acetate, 70% hexanes) to provide 540 mg (52%). of Example 3 as an off-white solid: mp 265–268° C. 1H NMR (DMSO-d₆): δ 11.23 (s, 1H), 7.54 (m, 2H), 7.44 (d, J=8 Hz, 1H), 7.33 (d, J=8 Hz, 1H), 7.18 (m, 2H), 7.05 (m, 2H), 6.73 (s, 1H), 6.51 (s, 1H), 4.39 (dd, J=4.11 Hz, 1H), 4.26 (d, J=17 Hz, 1H), 3.98 (d, J=17 Hz, 1H), 3.59 (dd, J=4.15 Hz, 1H), 3.02 (m, 4H). MS ES+m/e=386 (p+1). Anal. Calcd. for $C_{23}H_{19}N_3O_3$: C, 71.67; H, 4.96; N, 10.90. Found: C, 71.61; H, 4.82; N, 10.72.

Intermediate 3

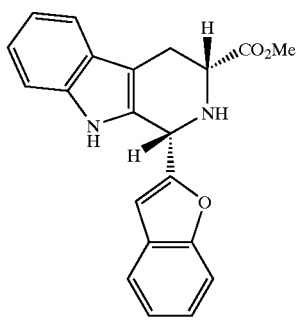

Preparation of (1R,3R)- and (1S,3R)-1-benzofuran-2-yl-2,3,4,9-tetrahydro-1H-p-carboline-3-carboxylic acid methyl ester (Intermediates 3 and 4). Condensation of (R)-(+)-tryptophan with benzo-furan-2-carbaldehyde produced Intermediates 3 and 4 by the same method described above for Intermediates 1 and 2. The crude mixture of diastereomers was separated by chromatography (Biotage 75M, 20% ethyl acetate/80% hexanes) to give 2.85 g (44%) of (1R,3R)-1-benzofuran-2-yl-2,3,4,9-tetrahydro-1H-β-carboline-3-carboxylic acid methyl ester (Intermediate 4) and 950 mg (15%) of (1S,3R)-1-benzofuran-2-yl-2,3,4,9-tetrahydro-1H-p-carboline-3-carboxylic acid methyl ester (Intermediate 3) as foams.

(1S,3R)-1-Benzofuran-2-yl-2,3,4,9-tetra-hydro-1H-β-carboline-3-carboxylic acid methyl ester (Intermediate 3): 1H NMR (DMSO-d₆): δ 10.66 (s, 1H), 7.64 (m, 1H), 7.25 (m, 3H), 7.02 (m, 2H), 6.88 (s, 1H), 5.55 (s, 1H), 3.93 (m, 1H), 3.67 (s, 3H), 3.03 (m, 1H), 2.82 (m, 1H); TOF MS ES+ exact mass calculated for $C_{21}H_{19}N_2O_3$ (p+1): m/z-347.1396. Found: 347.1369.

EXAMPLE 4

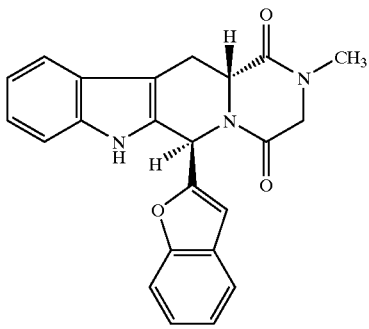

Example 4 was prepared in an identical is manner as Example 3 from Intermediate 4.

Intermediate 4

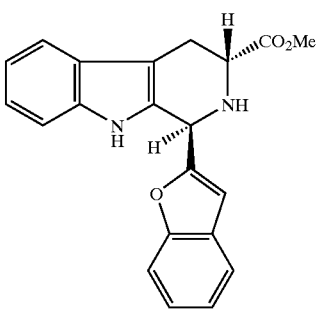

(1R,3R)-1-Benzofuran-2-yl-2,3,4,9-tetra-hydro-1H-β-carboline-3-carboxylic acid methyl ester (Intermediate 4): ¹H NMR (DMSO-d₆): δ 10.87 (s, 1H), 7.55 (5, J=7 Hz, 1H), 7.47 (d, J=7 Hz, 1H), 7.26 (m, 3H), 7.01 (m, 2H), 6.56 (s, 1H), 5.43 (s, 1H), 3.90 (m, 1H), 3.66 (s, 3H), 3.07 (dd, J=4.15 Hz, 1H), 2.80 (m, 1H); TOF MS ES+ exact mass calculated for $C_{20}H_{19}N_2O_3$ (p+1): m/z=347.1382. Found: 347.1382.

Preparation of Examples 5 and 6

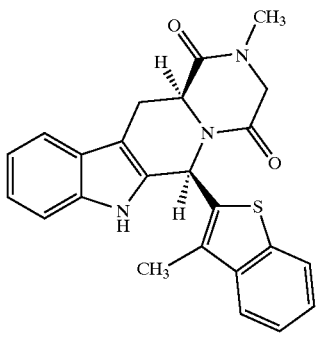

EXAMPLE 5

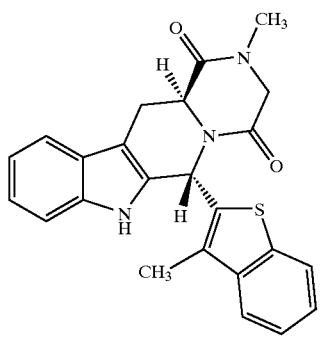

Example 5 was prepared from the following Intermediate 5. Example 6 was prepared from the following Intermediate 6.

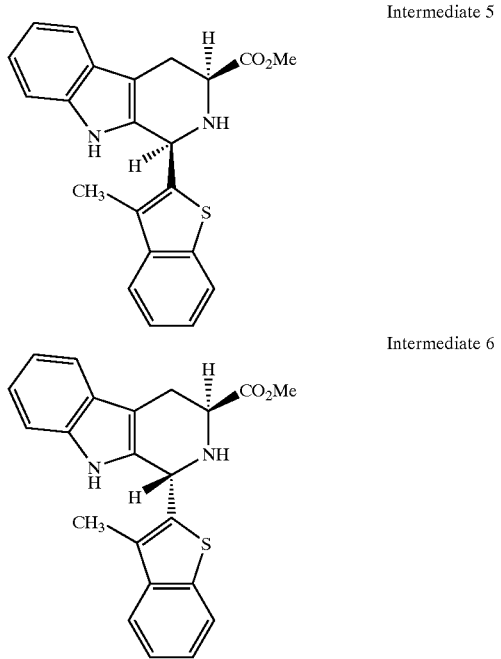

Intermediate 5

Intermediate 6

Preparation of (1R,3S)- and (1S,3S)-1-(3-methyl-benzo[b]thiophen-2-yl)-2,3,4,9-tetrahydro-1H-β-carboline-3-carboxylic acid methyl ester (Intermediates 5 and 6)

An aqueous solution of (S)-(−)-tryptophan hydrochloride (1.45 g, 5.7 mmol) was made alkaline with a saturated sodium bicarbonate solution and extracted with ethyl acetate. The extract was washed once with aqueous sodium chloride solution, dried (sodium sulfate), filtered, and concentrated in vacuo. The free base-was dissolved in chloroform (50 mL) and treated with 3-methylbenzo[b]thiophene-2-carbaldehyde (1.0 g, 5.7 mmol) and trifluoroacetic acid (21.2 mmol, 1.32 g). The resulting mixture then was heated to reflux for 3 hours. The solution was cooled to room temperature, washed once with saturated sodium bicarbonate solution, dried (sodium sulfate), filtered, and concentrated in vacuo to provide a mixture of two diastereomers. The isomers were separated by chromatography (silica gel, 30% ethyl acetate:hexanes) to give 700 mg (38%) of (1R,3S)-1-(3-methylbenzo[b]thiophen-2-yl)-2,3,4,9-tetrahydro-1H-β-carboline-3-carboxylic acid methyl ester (Intermediate 5) and 400 mg (19%) of (1S;3S)-1-(3-methylbenzo[b]thiophen-2-yl)-2,3,4,9-tetra-hydro-1H-β-carboline-3-carboxylic acid methyl ester (Intermediate 6).

Intermediate 5: $^1$H NMR (DMSO-$d_6$): δ 10.04 (s, 1H), 7.8–6.9 (m, 8H), 5.92 (d, J=2 Hz, 1H), 4.1 (dd, J=5.10 Hz, 1H), 3.65 (s, 3H), 3.45 (t, J=2 Hz, 1H), 3.03 (dq, J=5.15 Hz, 2H), 2.5 (s, 3H); MS ES+m/e 377.1 (p+1), ES−m/e 375.2 (p−1).

(1S,3S)-1-(3-Methylbenzo[b]thiophen-2-yl)-2,3,4,9-tetrahydro-1H-β-carboline-3-carboxylic acid methyl ester (Intermediate 6): $^1$H NMR (DMSO-$d_6$): δ 10.4 (s, 1H), 7.9–6.9 (m, 8H), 5.85 (br s, 1H), 4.0 (m, 1H), 3.75 (s, 3H), 3.0 (br s, 1H), 2.95 (dd, J=6.10 Hz, 2H), 2.5 (s, 3H); ME ES+m/e 377.1 (p+1), ES−m/e 375.2 (p−1).

Example 5, (6R,12aS)-2-methyl-6-(e-methyl-benzo[b]thiophen-2-yl)-2,3,6,7,12,12a-hexahydro-pyrazino[1',2':1,6]pyrido[3,4-b]indole-1,4-dione, was prepared by the same method given above for Example 1. The residue was dissolved in tetrahydrofuran (20 mL) and water (5 mL). A solution of 2M methylamine in tetrahydrofuran (5 mL, 20 mmol) was added and the reaction was heated at reflux for 30 minutes. After cooling to room temperature, the solvent was evaporated and the residue was diluted with ethyl acetate. A crystalline solid formed and was filtered to give 220 mg (20%) of Example 3 as a colorless solid: mp 230–234° C. $^1$H NMR (DMSO-$d_6$): δ 11.07 (s, 1H), 7.9–7.0 (m, 9H), 4.5 (dd, J=4.13 Hz, 1H), 4.2 (ABq, J=18.63 Hz), 3.35 (dd, J=4.13 Hz, 1H), 3.06 (dd, J=13.4 Hz, 1H), 2.82 (s, 3H), 2.56 (s, 3H); MS ES+m/e 416.1 (p+1), ES−m/e 414.2 (p−1); IR (KBr, cm$^{-1}$) 1728, 1677, 1649.

Example 6 was prepared in a manner identical to Example 5 from Intermediate 6.

Examples 7 and 8 are prepared in a manner identical to Examples 5 and 6 from Intermediates 7 and 8.

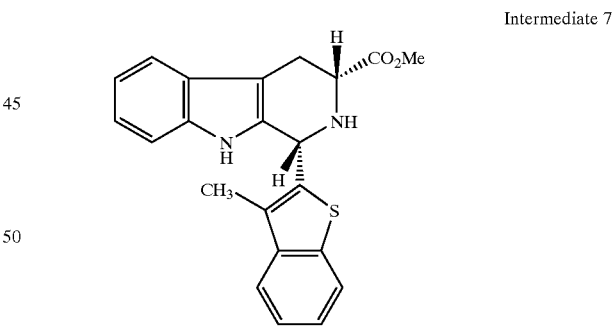

Intermediate 7

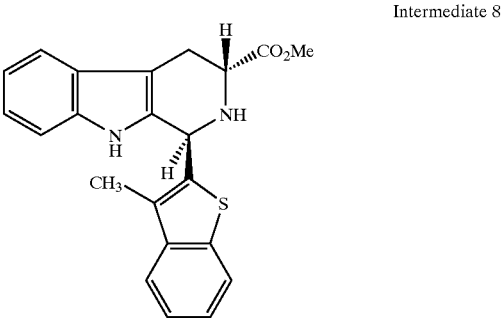

Intermediate 8

EXAMPLE 7

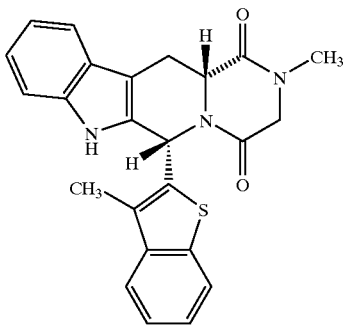

EXAMPLE 8

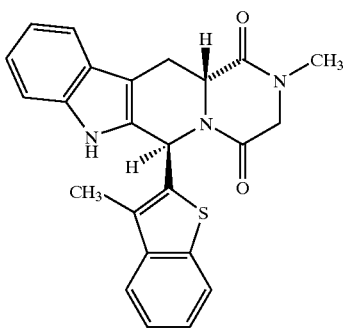

Preparation of (1S,3R)- and (1R,3R)-1-(3-Methyl-benzo[b]thiophen-2-yl)-2,3,4,9-tetrahydro-1H-β-carboline-3-carboxylic acid methyl ester (Intermediates 7 and 8)

An aqueous solution of (R)-(+)-tryptophan methyl ester hydrochloride (5.5 g, 19.6 mmol) was made basic with saturated sodium bicarbonate solution and extracted with ethyl acetate. The extract was washed with water, dried (magnesium sulfate), filtered, and concentrated in vacuo to produce a yellow oil (3.72 g). The free base was dissolved in chloroform (75 ml) followed by addition of 3-methylbenzo[b]thiophene-2-carboxaldehyde (3.0 g, 17.0 mmol) and trifluoroacetic acid (3.0 mL). The solution was stirred at 25° C. for 14 hours, and at reflux for 1 hour. The solution was cooled and diluted with ethyl acetate (200 mL). The solution was extracted three times with ethyl acetate (100 mL), then the combined extracts were dried (magnesium sulfate), filtered, and concentrated in vacuo to give two diastereomers. The isomers were separated by chromatography (silica gel, 20% ethyl acetate/80% hexanes) to give 1.92 g (30%) of (1S,3R)-1-(3-methylbenzo[b]thiophen-2-yl)-2,3,4,9-tetrahydro-1H-β-carboline-3-carboxylic acid methyl ester and 1.68 g (27%) of (1R,3R)-1-(3-methylbenzo[b]thiophen-2-yl)-2,3,4,9-tetrahydro-1H-p-carboline-3-carboxylic acid methyl ester.

Intermediate 7:
$^1$H NMR (DMSO-$d_6$) δ: 10.51 (s, 1H), 7.82 (t, J=6.22 Hz, 2H), 7.37 (m, 3H), 7.21 (d, J=6.95 Hz, 1H), 6.99 (q, J=8.14 Hz, 2H), 5.90 (s, 1H), 3.98 (m, 1H), 3.75 (s, 3H), 3.20 (m, 1H), 3.06 (m, 1H), 2.84 (m, 1H), 2.53 (s, 3H); MS ES+m/e 3.77.1 (p+1). Anal. Calcd. for $C_{22}H_{19}N_2O_2S$: C, 70,18; H 5.35; N 7.44.

Intermediate 8:
$^1$H NMR (DMSO-$d_6$) δ: 10.54 (s, 1H), 7.81 (d, J=8 Hz, 1H), 7.32 (m, 3H), 7.20 (d, J=7.6 Hz, 1H), 7.01 (m, 2H), 5.93 (s, 1H), 4.10 (m, 1H), 3.64 (s, 3H), 3.43 (m, 1H), 3.07 (dd, J=4, 15 Hz, 2H), 2.51 (s, 3H); MS ES+m/e 377.1 (p+1). Anal. Calcd. for $C22H_{19}N_2O_2S$: C, 70.18; H 5.35; N 7.44. Found: C, 69.93; H, 5.31; N 7.33.

Preparation of Example 7
(6R,12aR)-2-methyl-6-(3-methylbenzo[b]thiophen-2-yl)-2,3,6,7,12,12a-hexahydropyrazino[1'2':1,6]-pyrido[3,4-b]indole-1,4-dione (1R,3R)-1-(3-Methylbenzo[b]thiophen-2-yl)-2,3,4,9-tetrahydro-1H-β-carboline-3-carboxylic acid methyl ester (1.75 g, 4.6 mmol) was treated as described below in Example 8 to provide 540 mg (28%) of Example 7.
$^1$H NMR (DMSO-$d_6$) δ: 11.21 (s, 1H), 7.82 (d, J=8.05 Hz, 2H), 7.54 (d, J=7.68 Hz, 1H), 7.46 (m, 6H), 7.21 (m, 2H), 7.18 (m, 2H), 4.51 (dd, J=4.02, 11.7 Hz, 1H), 4.27 (d, J=17.9 Hz, 1H), 4.07 (d, J=17 Hz, 1H), 3.34 (m, 2H), 3.06 (dd, J=4.39, 19, 1H), 2.90 (s, 3H), 2.54 (s, 31H). TOF MS ES+ extract mass calculated for $C_{24}H_{22}N_3O_2S$ (p+1): m/z=416.1433. Found: 416.1558.

Preparation of Example 8

A solution of (1S,3R)-1-(3-methylbenzo[b]-thiophen-2-yl)-2,3,4,9-tetrahydro-1H-β-carboline-3-carboxylic acid methyl ester (1.50 g. 3.90 mmol) in tetrahydrofuran (25 mL) was treated with triethylamine (2.5 mL). Chloroacetyl chloride (0.50 g, 4.4 mmol) was added and the solution was heated at reflux for 18 hours. A few additional drops of chloroacetyl chloride were added to drive the reaction to completion. After cooling, deionized water (10 mL) and ethyl acetate (200 mL) were added, the organic layer separated, washed once with dilute hydrochloric acid, dried (magnesium sulfate), filtered, and concentrated in vacuo. The residue was dissolved in tetrahydrofuran (50 mL) and treated with 2.5 M methylamine (1.0 mL) in tetrahydrofuran. The resulting solution was refluxed for 2 hours, cooled to room temperature, diluted with water, and extracted with ethyl acetate. The solution was dried (magnesium sulfate), filtered, and concentrated in vacuo. Chromatography (silica gel, 15% ethyl acetate/85% hexane to 40% ethyl acetate/60% hexane) of the residue provided 0.57 g (34%) of the title product as a yellow solid.
$^1$H NMR (DMSO-d6) δ: 10.98 (s, 1H), 7.71 (m, 2H), 7.60 (d, J=6.95 Hz, 3H), 7.31 (m, 3H), 7.05 (m, 2H), 6.68 (s, 1H), 4.45 (dd, J=4.39, 11.71 Hz, 1H), 4.17 (d, J=18.66 Hz, 1H), 3.95 (d, J=17.56 Hz, 1H), 3.62 (dd, J=4.49, 15.73 Hz, 1H), 3.30 (d, J=7.31 Hz, 1H), 3.10 (m, 1H), 2.92 (s, 3H), 2.65 (s, 3H).

Preparation of Example 9

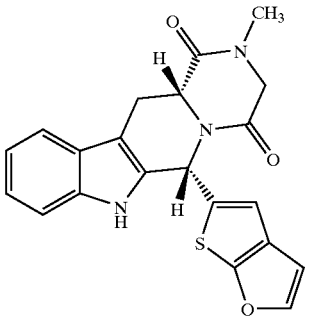

EXAMPLE 9

Example 9 was prepared from D-tryptophan methyl ester hydrochloride and thieno[2,3-b]furan-5-carboxaldehyde (Intermediate 9) as depicted in the synthetic following scheme. Intermediate 9 was synthesized in five steps from a starting acetal according to known procedures. See G. D. Hartman et al., *J. Heterocyclic Chem.*, 27, 679 (1990).

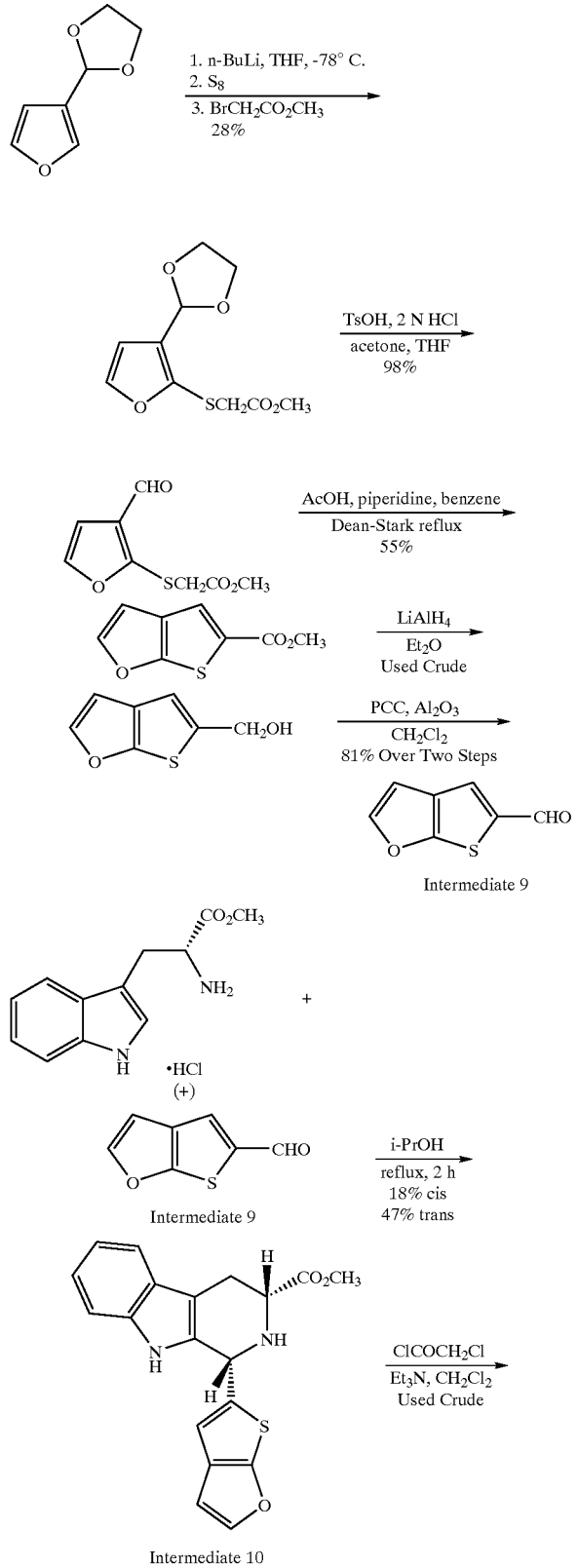

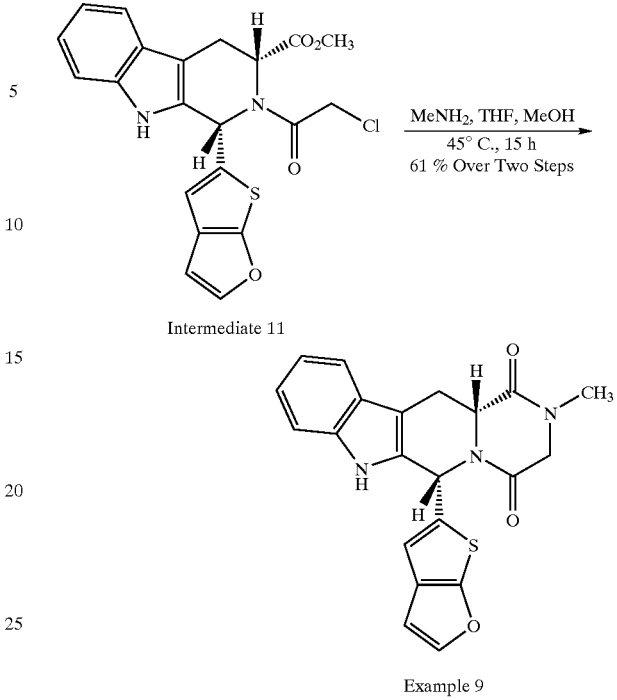

Intermediate 11

Example 9

EXAMPLE 9

Preparation of Methyl 3-[2-(1,3-Dioxolanyl)]-furan-2-yl mercaptoacetate

To a mechanically stirred solution of starting acetal (27.6 g, 197 mmol) in anhydrous THF (100 mL) under a nitrogen blanket at −78° C. was added n-butyllithium (126 mL, 201 mmol, 1.6 M solution in hexanes). The resulting light yellow slurry was stirred at −78° C. for 45 minutes after which sulfur (6.7 g, 209 mmol) was added in three portions over 5 minutes. The resulting orange slurry was stirred at −78° C. for 30 minutes, then at −50° C. for 20 minutes to provide a deep purple suspension which again was cooled to −78° C. A solution of methyl bromoacetate (22.4 g, 240 mmol) in THF (20 mL) was added dropwise over 10 minutes to afford a cloudy yellow mixture. After stirring at −78° C. for 30 minutes, the reaction mixture was allowed to gradually warm to −10° C. over 1.5 hours and stirred at −10° C. for an additional 20 minutes. The resulting brown, two-phase mixture was diluted with diethyl ether (500 mL), washed successively with brine (100 mL), water (2×75 mL), and brine (100 mL)), dried over $Na_2SO_4$, filtered and the solvent was removed under reduced pressure. The resulting residue was purified by flash column chromatography, eluting with hexanes/ethyl acetate (3:1), to provide the thioether as a yellow oil (11.4 g, 28%): TLC $R_f$ (4:1 hexanes/ethyl acetate)=0.28; $^1$H NMR (300 MHz, $CDCl_3$): δ: 7.48 (d, J=2.0 Hz, 1H), 6.51 (d, J=2.0 Hz, 1H), 5.87 (s, 1H), 4.15–3.90 (m, 4H), 3.69 (s, 3H), 3.50 (s, 2H) ppm.

Preparation of (3-Formylfuran-2-yl)mercaptoacetate

The above thioether (11.4 g, 47.0 mmol) and p-toluenesulfonic acid monohydrate (450 mg, 2.4 mmol) were stirred in a mixture of acetone (80 mL), THF (20 mL), and 2 N aqueous HCl (12 mL) at room temperature for 2 hours. The mixture was neutralized with a saturated $NaHCO_3$ solution, and the resulting suspension was concentrated to 20 mL under reduced pressure. The mixture was diluted with diethyl ether (300 mL), washed successively with water (30 mL), and brine (50 mL), dried over $Na_2SO_4$, filtered and the solvent was removed under reduced pressure to provide the aldehyde as a brown oil which was used without further purification (9.24 g, 98%): TLC $R_f$ (4:1 hexanes/ethyl acetate)=0.30; $^1$H NMR (300 MHz, $CDCl_3$): δ: 10.0 (s, 1H), 7.51 (d, J=2.0 Hz, 1H), (d, J=2.0 Hz, 1H), s, 5H) ppm.

Preparation of Methyl Thieno[2,3-b]furan-5-carboxylate

Piperidine (5.60 mL, 57.3 mmol) was added to a solution of acetic acid (3.57 mL, 62.4 mmol) in benzene (200 mL) and the mixture was stirred at room temperature for 15 minutes. To this cloudy mixture was added a solution of the above aldehyde (9.24 g, 46.2 mmol) in benzene (50 mL). The resulting red solution was refluxed with water removal via a Dean-Stark trap for 4.5 hours under a nitrogen blanket. The resulting brown solution was cooled to room temperature and diluted with ether (250 mL). The organic solution was washed successively with water (100 mL), 2 N aqueous HCl (30 mL), saturated $NaHCO_3$ solution, water (30 mL), and brine (50 mL), dried over $Na_2SO_4$, filtered and the solvent was removed under reduced pressure. The residue was purified by flash column chromatography, eluting with hexanes/ethyl acetate (5:1), to provide the thienofuran as a pink solid (4.6 g, 55%): TLC $R_f$(4:1 hexanes/ethyl acetate)= 0.79; $^1$H NMR (300 MHz, $CDCl_3$): δ: 7.72 (s, 1H), 7.66 (d, J=2.2 Hz, 1H), 6.74 (d, J=2.2 Hz, 1H), 3.90 (s, 3H) ppm.

Preparation of Thieno[2,3-b]furan-5-carboxaldehyde (Intermediate 9)

To a suspension of lithium aluminum hydride (436 mg, 11.5 mmol) in ether (60 mL) at 0° C. under a nitrogen blanket was added a solution of the above thienofuran (1.0 g, 5.49 mmol) in diethyl ether (20 mL) dropwise, after which the mixture was warmed to room temperature and stirred for 2 hours. The suspension was cooled to 0° C. and treated successively with water (0.5 mL), 6 N aqueous sodium hydroxide (1.3 mL), and water (2.3 mL). The resulting salt was removed by filtration under reduced pressure, washed with ether (3×50 ml) and the filtrate was dried over $Na_2SO_4$, filtered, and concentrated under reduced pressure to a volume of approximately 2 mL. This concentrated solution of thieno[2,3-b]furan-5-carbinol was diluted immediately with methylene chloride (50 mL) and used directly in the next step: TLC $R_f$ (3:1 hexanes/ethyl acetate)=0.20.

To the above methylene chloride solution of the carbinol was added pyridinium chlorochromate (1.77 g, 8.63 mmol), and neutral aluminum oxide (4.0 g). The resulting mixture was stirred at room temperature under a nitrogen blanket for 1.5 hours. The black slurry was filtered through a short plug of silica gel, eluting with diethyl ether (100 mL) followed by methylene chloride (100 mL) The filtrate was concentrated to afford Intermediate 9 as an oil which was used directly in the next step (674 mg, 81% over two steps): TLC $R_f$ (3:1 hexanes/ethyl acetate)=0.33; $^1$H NMR (300 MHz, $CDCl_3$): δ: 9.90 (s, 1H), 7.70 (d, J=2.0 Hz, 1H), 7.68 (s, 1H), 6.80 (d, J=2. 0 Hz, 1H) ppm.

Preparation of cis-β-carboline (Intermediate 10)

A mixture of Intermediate 1 (674 mg, 4.43 mmol) and D-tryptophan methyl ester hydrochloride (1.18 g, 4.64 mmol) was refluxed in isopropyl alcohol (15 mL) under a nitrogen blanket for 2 hours. The resulting yellow solution was cooled to room temperature and diluted with ethyl acetate (100 mL). The mixture was washed successively with saturated $NaHCO_3$ solution (15 mL), water (10 mL), and brine (10 mL), dried over $Na_2SO_4$, filtered, and the solvent was removed under reduced pressure. The residue was purified by flash column chromatography, eluting with hexanes/ethyl acetate (2:1), to provide Intermediate 10 as a white foam (285 mg, 18%): TLC $R_f$ (2:1 hexanes/ethyl acetate)=0.33, $^1$H NMR (300 MHz, DMSO-$d_6$): δ: 7.7–7.50 (m, 3H), 7.30–7.09 (m, 3H), 7.08 (s, 1H), 6.67 (d, J=2.4 Hz, 1H), 5.55 (s, 1H), 3.92–4.00 (m, 1H), 3.83 (s, 3H), 3.27–3.17 (m, 1H), 3.08–2.93 (m, 1H) ppm. The trans-β-carboline was also obtained as a light yellow solid, but was not characterized (736 mg, 47%): TLC $R_f$ (2,:1 hexanes/-ethyl acetate)=0.22.

Preparation of cis-2-Chloroacetyl-β-carboline (Intermediate 11)

Chloroacetyl chloride (0.079 mL, 1.03 mmol) was added dropwise to a mixture of Intermediate 2 (280 mg, 0.80 mmol) and triethylamine (0.14 mL, 1.03 mmol) in methylene chloride (8 mL) at 0° C. under a nitrogen blanket, and the resulting mixture was stirred at 0° C. for 2 hours. The solution was diluted with ethyl acetate (60 mL), washed with a saturated $NaHCO_3$ solution (10 mL), and brine (10 mL), and the solvent was removed under reduced pressure to provide Intermediate 11 as a pink foam (405 mg), which was used without further purification or characterization.

Preparation of Example 9

A mixture of the crude Intermediate 11 (405 mg) and methylamine (1.6 mL, 3.2 mmol, 2 M solution in THF) in methanol (7 mL) was heated at 45° C. under a nitrogen blanket for 15 hours. The resulting solution was concentrated under reduced pressure to provide a yellow solid which was stirred in methanol (5 mL) for 1 hour. The solid was isolated by filtration under reduced pressure, washed with methanol (5×1 mL), and dried in a vacuum oven at 60° C. for 17 hours to provide Example 9 as an off-white solid (189 mg, 61% over two steps): mp 275-278° C.; TLC $R_f$(5:1 methylene chloride/ethyl acetate)=0.22; $^1$H NMR (500 MHz, DMSO-$d_6$): δ: 11.20 (s, 1H), 7.82 (d, J=2.0 Hz, 1H), 7.62 (d, J=7.8 Hz, 1H), 7.35 (d, J=7.8 Hz, 1H), 7.11 (t, J=7.8 Hz, 1H), 7.04 (t, J=7.8 Hz, 1H), 6.77 (s, 1H), 6.73 (d, J=2.0 Hz, 1H), 6.60 (s, 1H), 4.38 (dd, J=11.7, 4.2 Hz, 1H), 4.23 (d, J=17.1 Hz, 1H), 3.99 (d, J=17.1 Hz, 1H), 3.55 .(dd, J=15.8, 4.6 Hz, 1H), 2.95–2.85 (m, 4H) ppm; ESI MS m/z 390 $[C_{21}H_{17}N_3O_3S$—H]$^+$; $[α]_D^{25°\ C.}$=+36.4 (c=0.25, DMSO) Anal. Calcd. for $C_{21}H_{17}N_3O_3S$: C, 64.43; H, 4.38; N, 10.73. Found: C, 64.24; H, 4.39; N, 10.54. The stereochemistry of Example 9 was confirmed to be the desired cis isomer by a series of NOE difference experiments: a positive NOE enhancement from the C12a proton at 4.38 ppm to the C6 proton at 6.60 ppm; a positive NOE enhancement from the C6 proton at 6.60 ppm to the C12a proton at 4.38 ppm.

EXAMPLE 10

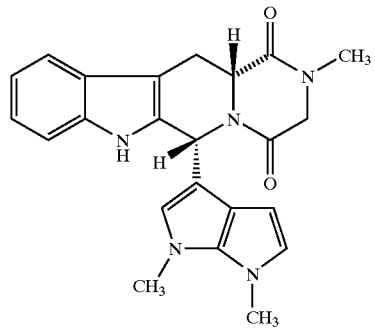

EXAMPLE 10

EXAMPLE 11

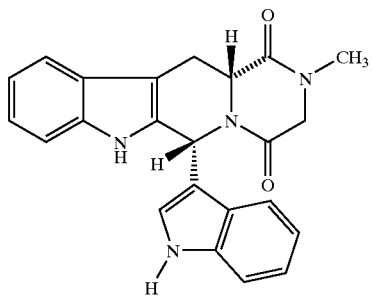

EXAMPLE 12

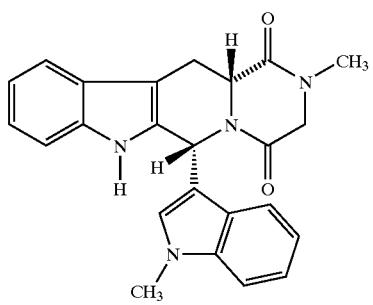

EXAMPLE 13

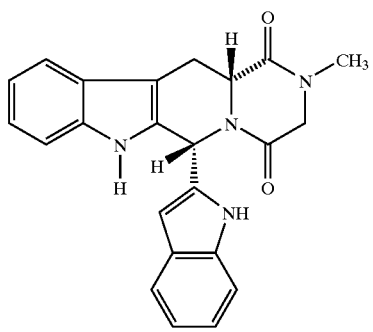

EXAMPLE 14

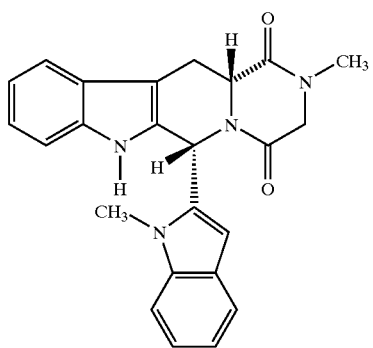

Preparation of Example 15

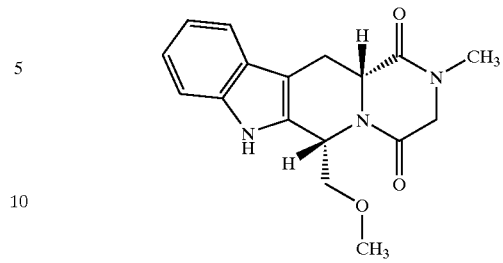

Example 15 was prepared from a tryptophan ester of structural formula (IV), wherein $R^0$ is hydrogen. The tryptophan ester utilized to prepare Example 15 is available commercially from Aldrich Chemical Co., Milwaukee, Wis.

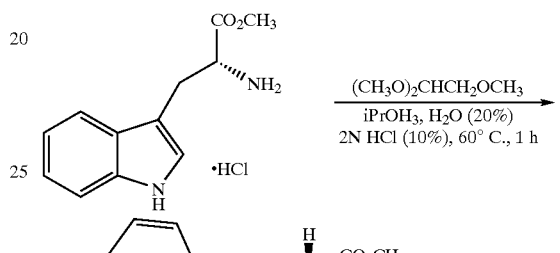

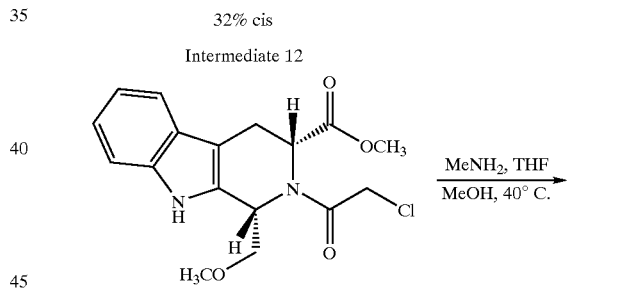

Intermediate 13

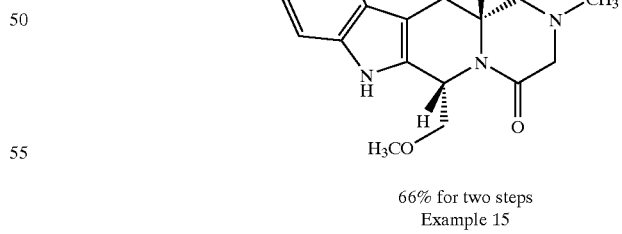

66% for two steps
Example 15

Intermediate 12
Preparation of a (+)-cis-β-carboline

A mixture of D-tryptophan methyl ester hydrochloride (1.27 g, 5.00 mmol), methoxyacetaldehyde dimethyl acetal (0.80 mL, 6.2 mmol) in isopropyl alcohol (12 mL) and water (2 mL) was stirred at 60° C. under a nitrogen blanket for 20 minutes. To the resulting clear solution was added 2N HCl (1 mL), and the resulting yellow solution stirred at 60° C. for 1 hour. The solution then was cooled to room temperature, diluted with ethyl acetate (100 mL), and neutralized with saturated aqueous sodium bicarbonate (NaHCO$_3$) (20 mL). The organic layer was washed with brine (20 mL), dried over sodium sulfate (Na$_2$SO$_4$), filtered, and the solvent was removed under reduced pressure to provide a yellow solid. The residue was purified by column chromatography, eluting with methylene chloride:ethyl acetate (4:1), to provide the (+)-cis carboline Intermediate 12 as a white solid (435 mg, 32%): TLC R$_f$ (4:1 methylene chloride/ethyl acetate)= 0.28; $^1$H NMR (300 MHz, CDCl$_3$): δ: 8.48 (bs, 1H), 7.50 (d, J=8.0 Hz, 1H), 7.34 (d, J=8.0 Hz, 1H), 7.20–7.03 (m, 2H), 4.42–4.34 (m, 1H), 3.87–3.54 (m, 6H), 3.50 (s, 3H), 3.20–3.10 (m, 1H), 2.90–2.76 (m, 1H). The trans carboline was incompletely eluted from the column: TLC R$_f$ (4:1 methylene chloride/ethyl acetate)=0.19.

Intermediate 13

Preparation of a (+)-cis-2-Chloroacetyl-β-carboline

Chloroacetyl chloride (0.15 mL, 1.90 mmol) was added dropwise to a mixture of Intermediate 12 (435 mg, 1.59 mmol) and triethylamine (0.27 mL, 1.90 mmol) in methylene chloride (18 mL) at 0° C. under a nitrogen blanket. The resulting mixture was stirred at 0° C. for 2 hours; after which the mixture was diluted with methylene chloride (50 mL) and washed successively with water (15 mL) and brine (15 mL). The organic layer was concentrated under reduced pressure to yield Intermediate 13 as a yellow foam (590 mg), which was used without purification. TLC R$_f$ (4:1 methylene chloride/ethyl acetate)=0.89.

Preparation of Examples 16–18

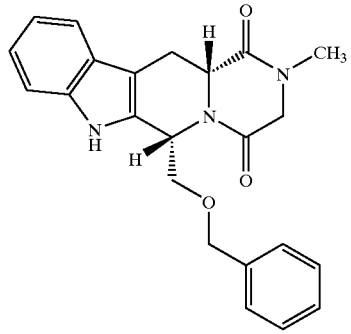

EXAMPLE 16

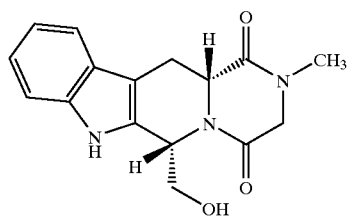

EXAMPLE 17

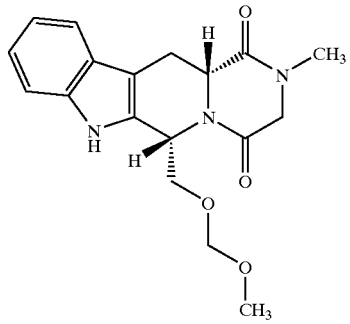

EXAMPLE 18

Examples 16–18 were prepared starting with the identical D-tryptophan methyl ester (D-Trp-OMeHCl) utilized in the preparation of Example 15, and with methoxyacetaldehyde dimethyl acetal by the following synthetic sequence.

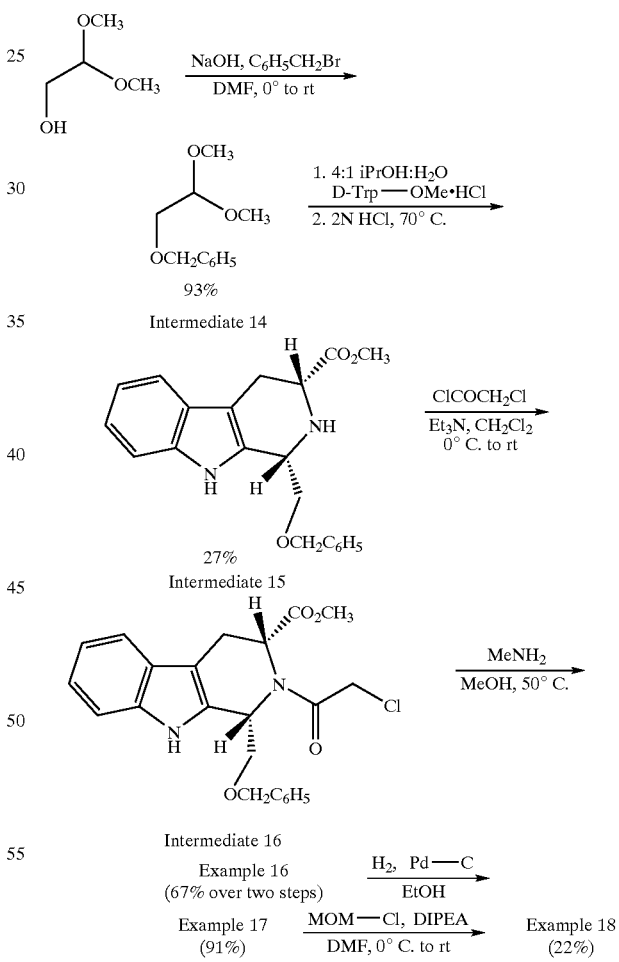

Intermediate 14
Preparation of a Dimethylacetal

A solution of methoxyacetaldehyde dimethylacetal (4.11 g, 38 mmol) and benzyl bromide (4.6 mL, 38 mmol) in N,N-dimethylformamide (17 mL) was cooled to 0° C. To this mixture was added sodium hydroxide pellets (1.66 g, 42 mmol), then the resulting mixture warmed slowly to room temperature overnight. The reaction mixture was poured into water and extracted with hexanes (2×200 mL). The combined organic extracts were washed with water, dried over $Na_2SO_4$, filtered, and concentrated under reduced pressure to yield Intermediate 14 as a pale yellow oil (7.03 g, 93%): $^1$H NMR (300 MHz, $CDCl_3$) δ: 7.28 (s, 5H), 4.52 (s, 2H), 4.49 (t, J=5.2 Hz, 2H), 3.44 (d, J=5.1 Hz, 1H), 3.32 (s, 6H).

Intermediate 15

Preparation of a cis-β-Carboline

D-tryptophan methyl ester hydrochloride (4.07 g, 16 mmol) and Intermediate 14 (3.75 g, 19 mmol) were combined with stirring in a solution of IPA (80 mL) and water (20 mL). To the resulting mixture was added 2N HCl (2 mL) and the resulting mixture heated at 70° C. for 18 hours. The mixture was neutralized with saturated aqueous $NaHCO_3$, then extracted with methylene chloride (2×400 mL). The combined organic extracts were dried over $Na_2SO_4$, filtered, and concentrated under reduced pressure. The residue was purified by flash column chromatography, eluting with methylene chloride/acetone (98:2), to provide the cis-carboline Intermediate 15 as an orange oil (1.5 g, 27%): TLC $R_f$ (6:1 methylene chloride/ethyl acetate)=0.49; $^1$H NMR (300 MHz, $CDCl_3$): δ: 8.46 (s, 1H), 7.50.(d, J=0.7 Hz, 1H), 7.47–7.25 (m, 6H), 7.18–7.06 (m, 2H), 4.65 (s, 2H), 4.44–4.39 (m, 2H), 3.88–3.82 (m, 1H), 3.81 (s, 3H), 3.66 (t, J=8.7 Hz, 1H), 3.18–3.11 (m, 1H), 2.88–2.78 (m, 1H), 1.87 (bs, 1H).

Intermediate 16

Preparation of a cis-2-Chloroacetyl-β-carboline

Chloroacetyl chloride (0.30 mL, 3.7 mmol) was added dropwise to a mixture of Intermediate 15 (1.0 g, 2.9 mmol) and triethylamine (0.52 mL, 3.7 mmol) in methylene chloride (25.mL) at 0° C. under an argon blanket. The resulting mixture was stirred at 0° C. for 2 hours, after which the mixture was slowly warmed to room temperature overnight. The resulting yellow solution was diluted with methylene chloride, then washed successively with water, saturated aqueous $NaHCO_3$ and brine. The organ-c layer was dried over $Na_2SO_4$, filtered, and the solvent was removed under reduced pressure to provide Intermediate 16 as a tan foam which was used without purification. (1.2 g): TLC $R_f$ (6:1 methylene chloride/ethyl acetate)=0.94.

EXAMPLE 16

Preparation of (6S,12aR)-6-Benzyloxymethyl-2-methyl-2,3,6,7,12,12a-hexahydropyrazino[1'2':1,6]pyrido-[3,4-b]indole-1,4-dione A mixture of crude Intermediate 16 (about 1.2 g, 2.8 mmol), methylamine (7.0 mL, 2.0 M in THF, 13.5 mmol), and methanol (25 mL) was heated at 50° C. under an argon blanket overnight. The resulting solution was cooled to room temperature. The solvent then was removed under reduced pressure to give an orange residue, which was purified by flash column chromatography, eluting with methylene chloride/ethyl acetate (5:1 to 2:1), to provide Example 11 as a pale yellow oil which crystallized under vacuum (0.83 g, 76%). A small sample was recrystallized from cold methylene chloride to give a white solid. The compound was confirmed to be the cis-isomer by NOE difference experiments (positive enhancement): mp 181–187° C.; TLC $R_f$ (4:1 methylene chloride/ethyl acetate)=0.29; $^1$H NMR (300 MHz, DMSO-$d_6$): δ: 11.06 (s, 1H), 7.56 (d, J=7.6 Hz, 1H), 7.37 (d, J=7.7 Hz, 1H), 7.21–7.19 (m, 3H), 7.11–6.99 (m, 4H), 5.40 (t, J=3.9 Hz, 1H), 4.30 (s, 2H), 4.24–4.17 (m, 2H), 3.93 (d, J=17.0 Hz, 1H), 3.68 (d, J=4.0 Hz, 2H), 3.43–3.36 (m, 1H), 2.93 (s, 3H), 2.89–2.80 (m, 1H); $^{13}$C NMR (75 MHz, DMSO-$d_6$): δ: 167.0, 166.8, 138.1, 135.1, 132.0, 127.9, 127.2, 126.9, 125.7, 120.8, 118.6, 117.7, 111.2, 106.8, 71.9, 71.3, 54.8, 51.5, 51.3, 32.8, 22.3 ppm; CI MS (methane) m/z 268 ($C_{15}H_{13}N_3O_2$+H$^+$); $[\alpha]_D^{25° C.}$=+45° C. (c=0.5, $CHCl_3$). Anal. Calcd. for $C_{23}H_{23}N_3O_3$: C, 70.93; H, 5.95; N, 10.79. Found: C, 70.54; H, 5.94; N, 10.60.

EXAMPLE 17

Preparation of (6S,12aR)-6-Hydroxymethyl-2-methyl-2,3,6,7,12,12a-hexahydropyrazino-[1'2':1,6]pyrido[3,4-b]indole-1,4-dione Example 16 (0.58 g, 1.5 mmol) was dissolved in ethanol (80 mL) and treated with a catalytic amount of 10% palladium on carbon (about 10% wet). The mixture was stirred under a hydrogen atmosphere at room temperature for 2.5 hours, after which the palladium catalyst was removed by vacuum filtration through a plug of Celite, elating with methanol. The solvents were removed under reduced pressure to provide a yellow oil which was triturated with methanol/diethyl ether to provide Example 17 as a pale yellow solid (0.4 g, 91%). A small portion of the sample was recrystallized from methanol: mp 275–280° C.; TLC $R_f$ (4:1:0.5 methylene chloride/ethylacetate/methanol)=0.44; $^1$H NMR (300 MHz, DMSO-$d_6$): δ: 10.98 (s, 1H), 7.52 (d, J=7.6 Hz, 1H), 7.34 (d, J=7.7 Hz, 1H), 7.08–6.97 (m, 2H), 5.20 (t, J=3.9 Hz, 1H), 4.86 (t, J=5.9 Hz, 2H), 4.21–4.14 (m, 2H), 3.95 (d, J=16.9 Hz, 1H), 3.65–3.62 (m, 2H), 3.39–3.32 (m, 1H), 2.92 (s, 3H), 2.85–2.77 (m, 1H); $^{13}$C NMR (75 MHz, DMSO-$d_6$): δ: 167.0, 166.8, 135.9, 132.6, 125.8, 120.6, 118.5, 117.6, 111.2, 106.5, 63.2, 54.9, 53.8, 51.6, 32.8, 22.6 ppm; CI MS (methane) m/z 300 ($C_{16}H_{17}N_3O_3$+H)$^+$; $[\alpha]_D^{25° C.}$=+131.1 (c=0.5, methanol). Anal. Calcd. for $C_{16}H_{17}N_3O_3$·0.25 $H_2O$: C, 63.25; H, 5.81; N, 13.83. Found: C, 63.01; H, 5.73; N, 13.69.

EXAMPLE 18

Preparation of (6S,12aR)-Methoxymethoxymethyl-2-methyl-2,3,6,7,12,12a-hexahydropyrazino-[1',2':1,6]pyrido [3,4-b]indole-1,4-dione A solution of Example 17 (0.2 g, 0.67 mmol) in N,N-dimethylformamide (10 mL) was cooled to 0° C. To this mixture was added successively diisopropylethylamine (DIPEA) (0.3 mL, 1.7 mmol) and chloromethyl methyl ether (MOM-Cl) (0.12 mL, 1.5 mmol). The resulting mixture was warmed slowly to room temperature overnight. The reaction mixture was poured into saturated aqueous $NaHCO_3$, and extracted with methylene chloride (3×100 mL). The combined organic extracts were washed with water and saturated aqueous ammonium chloride ($NH_4Cl$), dried over $Na_2SO_4$, filtered and concentrated under reduced pressure to yield Example 18 as a tan oil which solidified under vacuum. This residue was purified by flash column chromatography, eluting with methylene chloride/ethyl acetate/methanol (4:1:0.2), to provide Example 18 as a white solid (0.05 g, 22%). Recrystallization from cold methylene chloride/diethyl ether produced a white crystalline solid which was confirmed to be the cis-isomer by NOE difference experiments (positive enhancement): mp 180–185° C.; TLC $R_f$ (4:1:0.2 methylene chloride/ethyl acetate/methanol)=0.43. $^1$H NMR (300 MHz, Benzene-$d_6$) δ: 7.53 (d, J=7.4 Hz, 1H), 7.49 (s, 1H), 7.24–7.12 (m, 3H), 5.39–5.36 (m, 1H), 4.27–4.22 (m, 2H), 4.00–3.95 (m, 1H), 3.78–3.71 (m, 1H), 3.64–3.59 (m, 1H), 3.38–3.08 (m, 4H), 2.86 (s, 2H), 2.38 (s, 3H); $^{13}$C NMR (75 MHz, Benzene-$d_6$): δ: 167.1, 166.6, 136.9, 132.2, 122.7, 120.5, 119.7, 111.7, 108.5, 96.8, 69.9, 56.1, 55.1, 52.7, 52.4, 33.1, 30.5, 24.6 ppm; CI MS (methane) m/z 344 ($C_{18}H_{21}N_3O_4$+H)$^+$; $[\alpha]_D^{25° C.}$=+40.9 (c=0.32, benzene-$d_6$). Anal. Calcd. for $C_{18}H_{21}N_3O_4$: C, 62.96; H, 6.16; N, 12.24. Found: C, 62.94; H, 6.12; N, 12.14.

The following are additional examples of compounds of structural formula (I) that can be prepared by methods analogous to the preparation of Examples 1–18.

EXAMPLE 19

(+−,cis)-6-Isobutyl-2-methyl-2,3,6,7,12,12a-hexahydropyrazino[1'2':1,6]pyrido[3,4-b]indole-1,4-dione

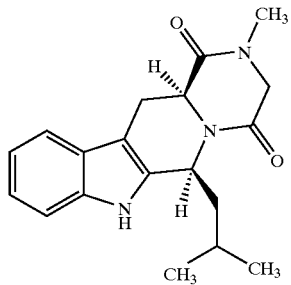

EXAMPLE 20

(+−, cis)-6–Cyclohexyl-2-methyl-2,3,6,7,12,12a-hexahydropyrazino[1'2':1,6]pyrido[3,4-b]indole,1,4-dione

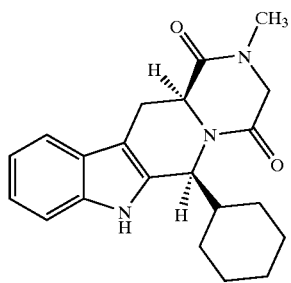

EXAMPLE 21

(+−, cis)-6–Cyclohex-3-enyl-2-methyl-2,3,6,7,12,12a-hexahydropyrazino[1'2':1,6]pyrido[3,4-b]indole-1,4-dione

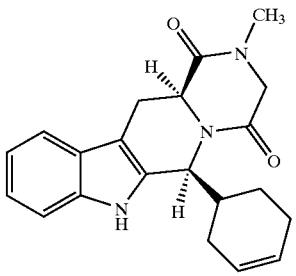

EXAMPLE 22

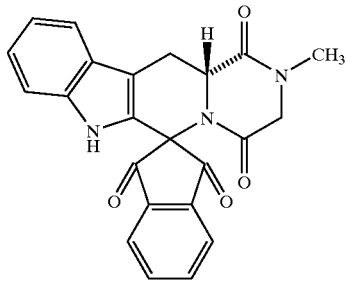

EXAMPLE 23

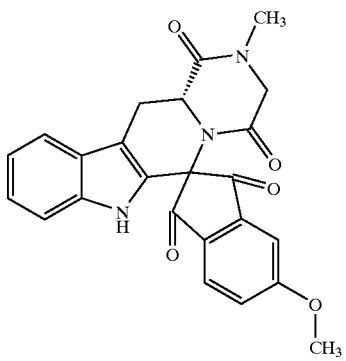

EXAMPLE 24

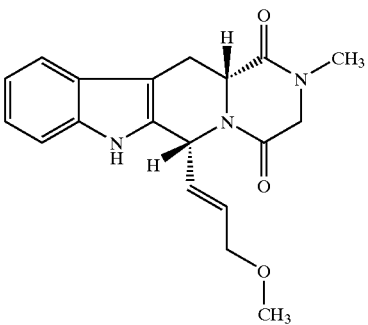

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 μM, and preferably less than about 25 μM, and more preferably less than about 15 μm. The compounds of the present invention typically exhibit an $IC_{50}$ value against recombinant human PDE5 of less than about 1 µM, and often less than about 0.05 µM. To achieve the full advantage of the present invention, a present PDE5 inhibitor has an $IC_{50}$ of about 0.1 nM to about 15 µM.

The production of recombinant human PDEs and the $IC_{50}$ determinations can be accomplished by well-known methods in the art. Exemplary methods are described as follows:

Expression of Human PDEs

Expression in *Saccharomyces cerevisiae* (Yeast)

Recombinant production of human PDE1B, PDE2, PDE4A, PDE4B, PDE4C. PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2–54 deposited on Aug. 31, 1998 with the American Type Culture Collection, Manassas, Va., under accession number ATCC 74465. Transformed host cells were grown in 2× SC-leu medium, pH 6.2, with trace metals, and vitamins. After 24 hours, YEP medium-containing glycerol was added to a final concentration of 2× YET/3% glycerol. Approximately 24 hr later, cells were harvested, washed, and stored at −70° C.

Human Phosphodiesterase Preparations

Phosphodiesterase Activity Determinations

Phosphodiesterase activity of the preparations was determined as follows. PDE assays utilizing a charcoal separation technique were performed essentially as described in Louahney et al. (1996). In this assay, PDE activity converts [32P]cAMP or [32P]cGMP to the corresponding (32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 µL reaction mixture containing (final concentrations) 40 mM Tris HCl (pH 8.0), 1 µM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) µg of Crotalus atrox venom then was added; and the incubation was continued for 3 minutes (15 minutes total). The reaction was stopped by addition of 200 µL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 MM $MgCl_2$, 0.25 mM DTT, 1 mM benzamidine, and 10 µM $ZnSO_4$). Cells were lysed in a Microfluidizer® (Microfluidics Corp.) using nitrogen at 20,000 psi. The lysate was centrifuged and filtered through 0.45 µm disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM $MgCl_2$, 0.25 mM DTT, 10 µM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 µM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 µM $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 µmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 µg/ml 5'-Nucleotidase,1 mM ECTA, and 0.15 µM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 µM. Tests against other PDE enzymes using standard methodology showed that compounds of the invention are selective for the cGMP-specific PDE enzyme.

Biological Data

The compounds according to the present invention were typically found to exhibit an $IC_{50}$ value of less than 500 nM. An in vitro test data for representative compounds of the invention is given in the following table:

TABLE 1

| Example | PDE5 $IC_{50}$ (nM) |
|---|---|
| 1 | 130 |
| 2 | 8726 |
| 3 | 16 |
| 4 | 880 |
| 5 | 25 |
| 6 | 40 |
| 7 | 1570 |
| 8 | 1 |
| 9 | 12 |
| 15 | 333 |
| 16 | 1,500 |
| 17 | 23,000 |
| 18 | 195 |
| 19 | 4,800 |
| 20 | 230 (bovine aorta) |
| 21 | 560 |

In vitro results

Obviously, many modifications and variations of the invention as hereinbefore set forth can be made without departing from the spirit and scope thereof, and, therefore, only such limitations should be imposed as are indicated by the appended claims.

What is claimed is:
1. A compound having a formula

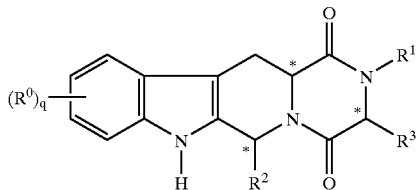

wherein R⁰, independently, is selected from the group consisting of halo and $C_{1-6}$alkyl;

$R^1$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl, and heteroaryl$C_{1-3}$alkyl;

$R^2$ is selected from the group consisting of hydrogen, $C_{1-6}$alkyl, $C_{1-3}$alkenylaryl, halo$C_{1-6}$alkyl, $C_{1-4}$alkyleneC(=O)OR$^a$, $C_{1-4}$alkyleneC(=O) NR$^a$R$^b$, $C_{3-8}$cycloalkyl, Het, $C_{3-8}$cycloalkenyl, $C_{3-8}$heterocycloalkenyl, $C_{1-4}$alkyleneHet, $C_{1-4}$alkyleneQR$^a$, $C_{2-6}$alkenyleneQR$^a$, $C_{1-4}$alkyleneQC$_{1-4}$alkyleneQR$^a$,

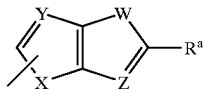 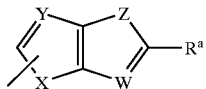

and a spiro substituent having the structure

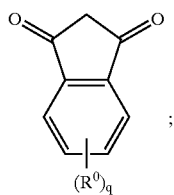

$R^3$ is selected from the group consisting of hydrogen and $C_{1-6}$alkyl, $R^a$ and $R^b$, independently, are selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, $C_{1-3}$alkyleneheteroaryl, and Het;

$R^c$ is null or is selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, $C_{1-3}$alkyleneheteroaryl, and Het;

Het is a 5- or 6-membered heterocyclic group, saturated or partially unsaturated, containing at least one heteroatom selected from the group consisting of oxygen, nitrogen, and sulfur, and optionally substituted with $C_{1-4}$alkyl or C(=O)OR$^a$;

Q is O, S, or NR$^a$;
W is O, S, or NR$^c$;
X is O, S, or NR$^a$;
Y is CR$^a$ or N;
Z is CR$^a$, G(R$^a$)₂, or NR$^a$; and
q is 0, 1, 2, 3, or 4, or a pharmaceutically acceptable salt or hydrate thereof.

2. The compound of claim 1 represented by the formula

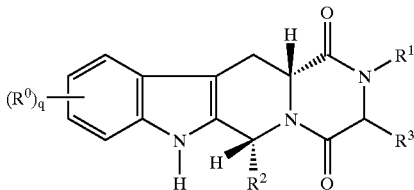

or a pharmaceutically acceptable salt or hydrate thereof.

3. The compound of claim 1 wherein R⁰ is hydrogen.

4. The compound of claim 1 wherein $R^1$ is selected from the group consisting of hydrogen, $C_{1-4}$alkyl, halo$C_{1-4}$alkyl, optionally substituted benzyl, $C_{3-6}$cycloalkylmethyl, pyridyl$C_{1-3}$alkyl, and furyl$C_{1-3}$alkyl.

5. The compound of claim 1 wherein $R^3$ is hydrogen.

6. The compound of claim 1 wherein $R^2$ is selected from the group consisting of hydrogen, $C_{1-6}$alkyl, $C_{1-3}$alkenylaryl, $C_{3-6}$cycloalkyl, Het, $C_{3-6}$cycloalkenyl, $C_{1-3}$alkyleneHet, $C_{1-4}$alkyleneQR$^a$, $C_{2-4}$alkenyleneQR$^a$, $C_{1-4}$alkyleneQC$_{1-4}$alkyleneQR$^a$,

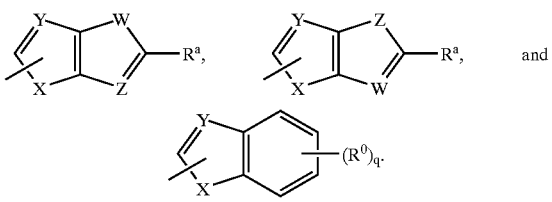

7. The compound of claim 1 wherein $R^2$ is selected from the group consisting of

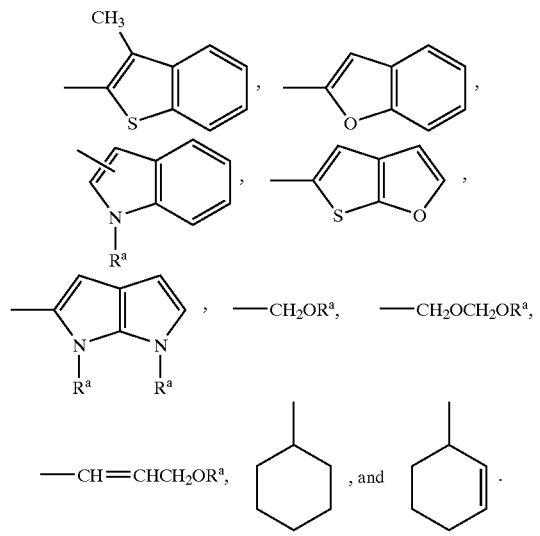

8. The compound of claim 7 wherein R$^a$ is selected from the group consisting of hydrogen, $C_{1-6}$alkyl, and benzyl.

9. A compound selected from the group consisting of
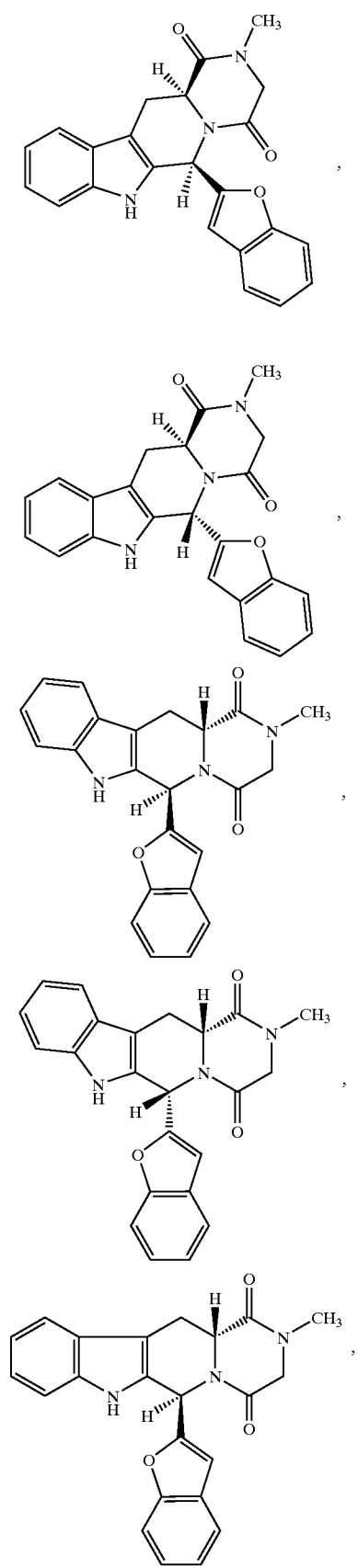
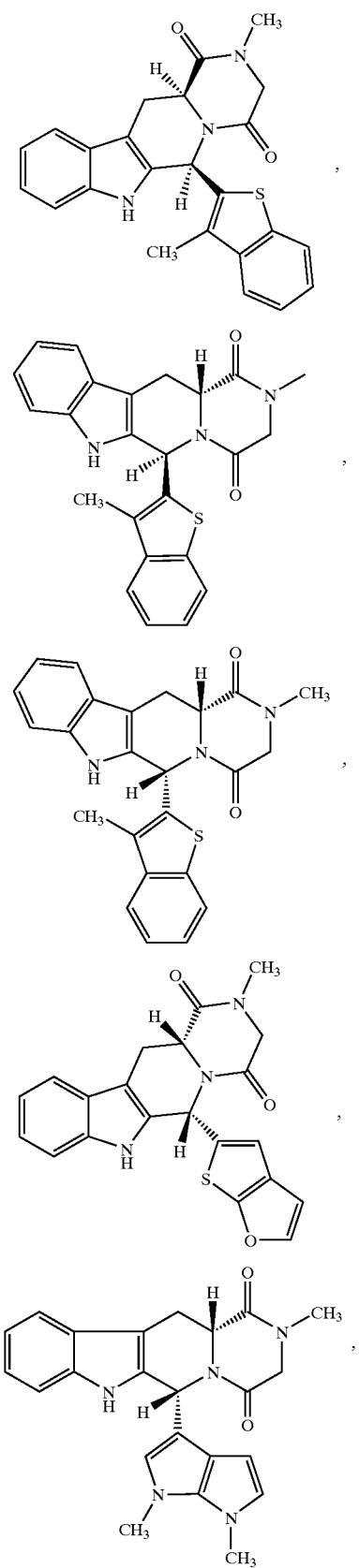

-continued
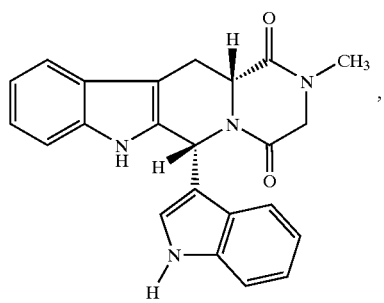
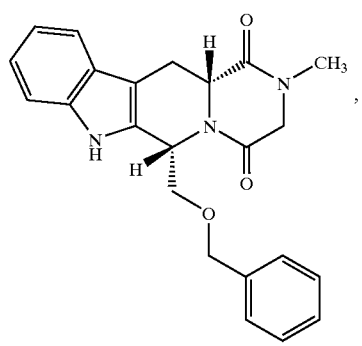
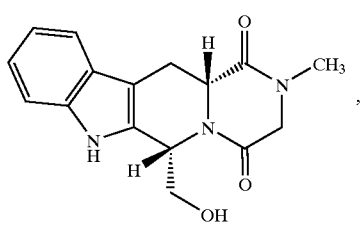
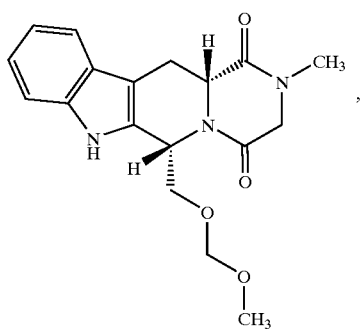
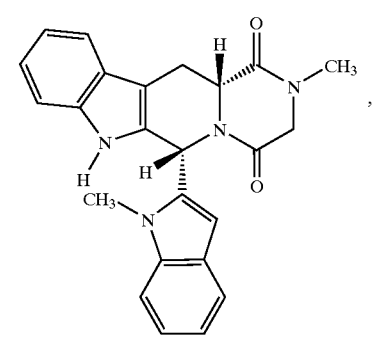
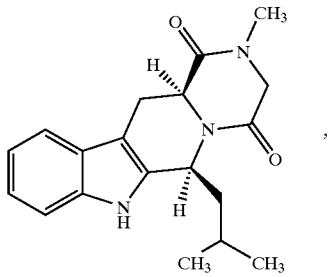
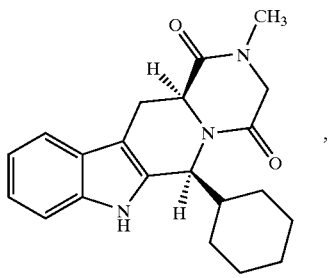
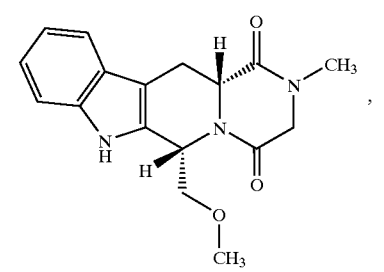

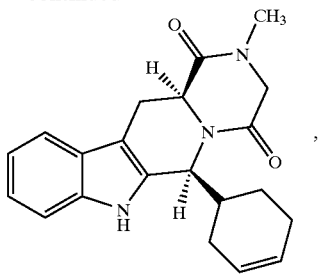

,

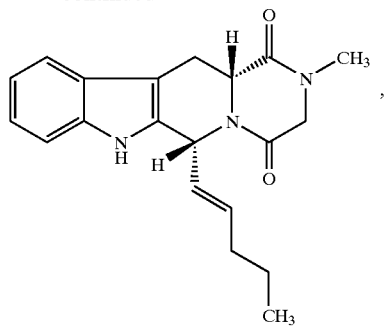

, or a pharmaceutically acceptable salt or hydrate thereof.

10. A pharmaceutical composition comprising a compound of claim 1, together with a pharmaceutically acceptable diluent or carrier.

11. A method of treating a male or female animal for a condition selected from the group consisting of male erectile dysfunction, female arousal disorder, and hypertension comprising administering to said animal an effective amount of a pharmaceutical composition comprising a compound of claim 1, together with a pharmaceutically acceptable diluent or carrier.

12. The method of claim 11 wherein the condition is male erectile dysfunction.

13. The method of claim 12 wherein the treatment is an oral treatment.

14. The method of claim 11 wherein the condition is female arousal disorder.

15. The method of claim 14 wherein the treatment is an oral treatment.

16. A method of treating a hypertension, in a human or a nonhuman animal body, comprising administering to said body a therapeutically effective amount of a compound of claim 1, or a pharmaceutically acceptable salt or hydrate thereof.

17. The method of claim 16 wherein the hypertension is pulmonary hypertension, or malignant hypertension.

18. A method for the treatment of male erectile dysfunction or female arousal disorder, comprising administration of an effective dose of a compound of claim 1, or a pharmaceutically acceptable salt or hydrate thereof, to an animal.

* * * * *

UNITED STATES PATENT AND TRADEMARK OFFICE
CERTIFICATE OF CORRECTION

PATENT NO. : 6,962,918 B2
APPLICATION NO. : 10/363569
DATED : November 8, 2005
INVENTOR(S) : Orme et al.

It is certified that error appears in the above-identified patent and that said Letters Patent is hereby corrected as shown below:

TITLE Page ITEM (54) AND COLUMN 1, LINES 1-2, "[1'2';1,6]" should be -- 1'2':1,6] -- and "4-B]" should be -- 4-b]--

Column 1, line 54, "$C_{1-4}alkyleneC(=O)-NR^aR^b$" should be -- $C_{1-4}alkyleneC(=O)NR^aR^b$ --

Column 2, line 1, "Spiro" should be --spiro--

Column 2, line 40, "bicyclo[2.2.1.]-heptyl" should be -- bicyclo[2.2.1.]heptyl --

Column 11, line 36, "constituent." should be -- constituent- -

Column 12, line 23, "synthetic-route" should be -- synthetic route --

Column 12, line 29, "with." should be -- with --

Column 14, line 66, "50%.ethyl" should be -- 50% ethyl --

Column 15, line 29, "(52%)." should be -- (52%) --

Column 15, line 54, "-1H-p-" should be -- -1H-β- --

Column 15, line 64, "-1H-p-" should be -- -1H-β- --

Column 16, line 4, "C21H$_{19}$N$_2$O$_2$" should be -- $C_{21}H_{19}N_2O_2$ --

Column 16, 3rd structure, insert -- Example 5 -- under the structure

Column 17, 1st structure, delete "EXAMPLE 5" above structure, then beneath the first structure insert -- Example 6 --

Column 17, line 15, "base-was" should be -- base was --

UNITED STATES PATENT AND TRADEMARK OFFICE
CERTIFICATE OF CORRECTION

PATENT NO. : 6,962,918 B2
APPLICATION NO. : 10/363569
DATED : November 8, 2005
INVENTOR(S) : Orme et al.

It is certified that error appears in the above-identified patent and that said Letters Patent is hereby corrected as shown below:

Column 18, line 1, "tetra-hydro" should be -- tetrahydro --

Column 18, line 10, "[b)" should be -- [b] --

Column 19, line 56, "p-carboline" should be -- β-carboline --

Column 19, line 62, "3.77.1" should be -- 377.1 --

Column 20, line 2, "C22H$_{19}$N$_2$O$_2$S" should be -- C$_{22}$H$_{19}$N$_2$O$_2$S --

Column 20, line 17, "(s, 31H)" should be -- (s, 3H) --

Column 24, line 8, "hexanes/-ethyl" should be -- hexanes/ethyl --

Column 29, line 34, "(25.mL)" should be -- (25 mL) --

Column 29, line 38, "organ-c" should be -- organic --

Column 30, line 16, "elating" should be -- eluting --

Column 33, line 52, "750xg" should be -- 750 X g --

Column 33, line 68, "5 MM" should be -- 5 mM --

Column 34, line 24, "ECTA" should be -- EGTA --

Column 36, line 1, "G(R$^a$)$_2$" should be -- C(R$^a$)$_2$ --

UNITED STATES PATENT AND TRADEMARK OFFICE
CERTIFICATE OF CORRECTION

PATENT NO. : 6,962,918 B2  Page 3 of 3
APPLICATION NO. : 10/363569
DATED : November 8, 2005
INVENTOR(S) : Orme et al.

It is certified that error appears in the above-identified patent and that said Letters Patent is hereby corrected as shown below:

Column 41, 3rd structure,

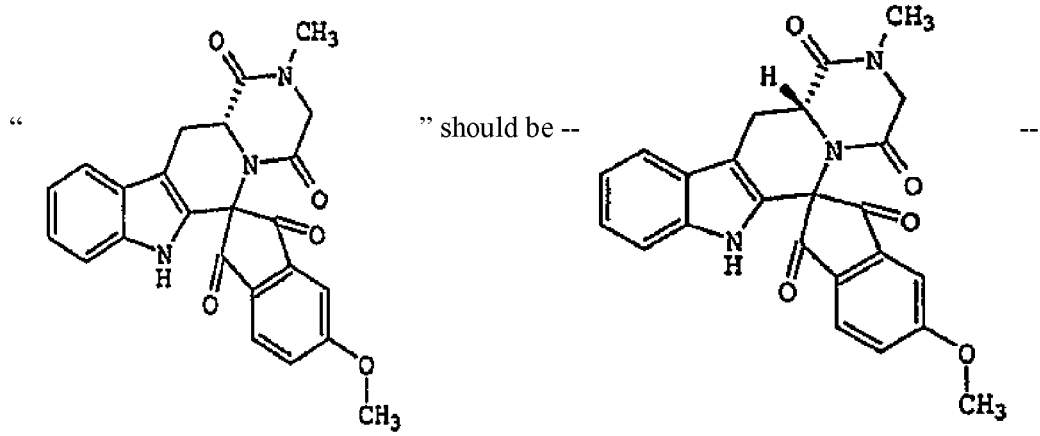

Signed and Sealed this

Twenty-sixth Day of December, 2006

JON W. DUDAS
*Director of the United States Patent and Trademark Office*